(12) United States Patent
Jones et al.

(10) Patent No.: US 9,752,705 B2
(45) Date of Patent: Sep. 5, 2017

(54) FLUID CONDUIT

(75) Inventors: Martin Peter William Jones, Chichester (GB); Charles Alexander Tavner, London (GB); Alan David Parker, Oxfordshire (GB); John Francis Gregg, Oxford (GB)

(73) Assignees: Magma Global Limited, Portsmouth (GB); Salunda Limited, Bicester (GB)

( * ) Notice: Subject to any disclaimer, the term of this patent is extended or adjusted under 35 U.S.C. 154(b) by 336 days.

(21) Appl. No.: 14/116,260

(22) PCT Filed: May 10, 2012

(86) PCT No.: PCT/GB2012/000424
§ 371 (c)(1),
(2), (4) Date: Mar. 24, 2014

(87) PCT Pub. No.: WO2012/153090
PCT Pub. Date: Nov. 15, 2012

(65) Prior Publication Data
US 2014/0182737 A1    Jul. 3, 2014

(30) Foreign Application Priority Data
May 10, 2011    (GB) .................................. 1107751.8

(51) Int. Cl.
*F16L 55/00*    (2006.01)
*F16L 9/14*    (2006.01)
(Continued)

(52) U.S. Cl.
CPC .................. *F16L 9/14* (2013.01); *G01F 1/32* (2013.01); *G01F 1/44* (2013.01); *G01F 1/58* (2013.01);
(Continued)

(58) Field of Classification Search
USPC .......................................... 138/153, 104, 44
See application file for complete search history.

(56) References Cited

U.S. PATENT DOCUMENTS

| | | | | |
|---|---|---|---|---|
| 1,865,795 A | * | 7/1932 | Schnitter ................... | G01F 1/42 |
| | | | | 138/44 |
| 3,142,960 A | * | 8/1964 | Bluck ..................... | F02K 9/974 |
| | | | | 138/44 |

(Continued)

FOREIGN PATENT DOCUMENTS

| CN | 1788189 A | 6/2006 |
|---|---|---|
| CN | 102012245 A | 4/2011 |

(Continued)

OTHER PUBLICATIONS

International Search Report and Written Opinion received in corresponding PCT Application No. PCT/GB2012/000424, dated Nov. 2012.

(Continued)

*Primary Examiner* — James Hook
(74) *Attorney, Agent, or Firm* — Levy & Grandinetti

(57) ABSTRACT

A fluid conduit (2) comprises a wall (4) defining a fluid flow path (6) and a confinement feature (24) within the wall (4) and being configured to confine energy within a cavity (26), wherein at least a portion of the fluid flow path (6) extends through the cavity (26). The confinement feature (24) may be configured to confine electromagnetic energy. The fluid conduit (2) may comprise an oscillator defined by the cavity (26) and a positive feedback arrangement (34). The fluid conduit (2) may be configured for sensing a property of a fluid present in or flowing through the fluid conduit (2) or for use in sensing a property of a fluid present in or flowing through the fluid conduit (2). More specifically, the present invention deals with a microwave cavity sensor wherein the (Continued)

cavity member (24) is embedded in the wall (4) of the fluid conduit (2), the wall (4) including a composite region (20).

36 Claims, 11 Drawing Sheets

(51) Int. Cl.
    *G01N 22/00*     (2006.01)
    *G01N 29/22*     (2006.01)
    *G01F 1/58*     (2006.01)
    *G01F 1/32*     (2006.01)
    *G01F 1/44*     (2006.01)
    *G01F 1/66*     (2006.01)
    *G01F 15/14*     (2006.01)

(52) U.S. Cl.
    CPC ............ *G01F 1/66* (2013.01); *G01F 15/14* (2013.01); *G01N 22/00* (2013.01); *G01N 29/222* (2013.01)

(56) References Cited

U.S. PATENT DOCUMENTS

| | | | | |
|---|---|---|---|---|
| 3,145,529 | A * | 8/1964 | Maloof | F02K 9/974 138/44 |
| 3,187,502 | A * | 6/1965 | Stover | F02K 9/974 138/155 |
| 3,189,676 | A | 6/1965 | Muller | |
| 3,200,585 | A * | 8/1965 | Climent | F02K 9/974 138/44 |
| 3,382,493 | A * | 5/1968 | Loper, Jr. | G01M 3/18 138/104 |
| 4,546,649 | A | 10/1985 | Kantor | |
| 4,774,872 | A * | 10/1988 | Creedon | F41B 6/00 138/153 |
| 4,974,245 | A | 11/1990 | Mioque et al. | |
| 5,046,854 | A | 9/1991 | Weller | |
| 5,051,034 | A * | 9/1991 | Goodman | B29C 47/0019 138/104 |
| 5,222,769 | A * | 6/1993 | Kaempen | B29C 70/207 138/128 |
| 5,518,034 | A * | 5/1996 | Ragout | B63B 27/24 138/103 |
| 5,699,835 | A * | 12/1997 | Nakagawa | F16L 9/133 138/141 |
| 5,861,561 | A * | 1/1999 | Van Cleve | G01F 1/8404 73/202 |
| 6,630,221 | B1 * | 10/2003 | Wong | C08J 9/00 264/176.1 |
| 2004/0173030 | A1 | 9/2004 | Harman | |
| 2005/0131387 | A1 | 6/2005 | Pursley | |
| 2011/0056306 | A1 | 3/2011 | Yamamoto | |
| 2013/0248039 | A1 * | 9/2013 | Bourlart | F16L 59/135 138/104 |

FOREIGN PATENT DOCUMENTS

| | | |
|---|---|---|
| DE | 2 040 682 | 2/1972 |
| EP | 0 581 017 | 2/1994 |
| EP | 0581017 A1 | 2/1994 |
| EP | 0684457 | 11/1995 |
| EP | 0 895 066 | 2/1999 |
| EP | 0895066 A1 | 2/1999 |
| EP | 1 574 828 | 9/2005 |
| EP | 1574828 A2 | 9/2005 |
| EP | 2 067 006 | 3/2008 |
| GB | 1578125 A | 11/1980 |
| IE | 82102 | 2/2002 |
| JP | 2010038752 | 2/2010 |
| WO | 2009/118569 | 10/2009 |
| WO | 2009/118569 A1 | 10/2009 |

OTHER PUBLICATIONS

Search Report received in corresponding GB Application No. GB1107751.8, dated Aug. 15, 2011.

Search Report in counterpart EP Appl. EP 15168973, dated Sep. 22, 2015.

Office Action in counterpart Chinese Appl. 201280033993.1, dated Sep. 30, 2015.

Yu, Z.Z. et al., "Electromagnetic inductance tomography (EMT): sensor, electronics and image reconstruction algorithm for a system with a rotatable parallel excitation field," IEE Proceedings, Science, Measurement and Technology, vol. 145, Jan. 6, 2998, pp. 20-25.

European Patent Office Examination Report of Sep. 26, 2016, for PCT/GB2012/000424.

English Translation for Second Office Action of Jun. 15, 2016, for Chinese PCT National Phase Patent Application No. 201280033993.1 dated May 10, 2012 (Publication No. 103703358A dated Apr. 2, 2014).

* cited by examiner

FLUID CONDUIT

FIELD

The present invention relates to a fluid conduit for use in imparting energy to a fluid present in of flowing therethrough and, in particular, though not exclusively, for sensing a property of the fluid.

BACKGROUND

It is known to determine various characteristics of a fluid from the measurement of electromagnetic or acoustic properties of the fluid. For example, WO2009/118569 discloses a Robinson oscillator sensor apparatus comprising a cavity member which contains a fluid and defines a resonant cavity for an electromagnetic field that extends into the fluid. The sensor apparatus may be used for identifying the fluid and/or determining a composition of the fluid according to the Robinson principle in which knowledge of both a resonant frequency and an electromagnetic loss in the cavity may provide an indication of whether a property of a fluid present in the cavity is within a prescribed parameter range regardless of the quantity of fluid present in the cavity. Knowledge of both the resonant frequency and loss may provide an indication of the quantity of fluid present in the cavity regardless of whether a property of a fluid present in the cavity is known to be within a prescribed range of parameters.

In such known methods for determining the characteristics of the fluid, the cavity member and/or coupling elements for coupling signals between RF electronic components of the sensor and the electromagnetic field may not operate reliably or may lack robustness in a demanding environment such as a downhole environment. For example, entrained solids or particulates in the fluid may clog or damage the cavity member and/or the coupling elements thereby impairing measurement sensitivity. For hydrocarbon fluids, deposition of contaminants or substances such as hydrates on the cavity member and/or the coupling elements may also impair measurement sensitivity. Such problems may be exacerbated by high fluid pressures and/or temperatures. Cavity members and/or coupling elements that extend into the cavity may also present an obstruction to fluid flow through the sensor. This may block or at least partially restrict the movement in or through the cavity of particulates, solids and/or the like entrained within the fluid. Additionally or alternatively, this may lead to an undesirable drop in fluid pressure.

SUMMARY

An aspect of the present invention relates to a fluid conduit for use in imparting energy to a fluid present in or flowing therethrough, the fluid conduit comprising:

a wall defining a fluid flow path and comprising a composite material formed of at least a matrix and one or more reinforcing elements embedded within the matrix; and a confinement feature within the wall and being configured to confine energy within a cavity, wherein at least a portion of the fluid flow path extends through the cavity.

Another aspect of the present invention relates to a fluid conduit for use in imparting energy to a fluid present in or flowing therethrough, the fluid conduit comprising:

a wall defining a fluid flow path; and a confinement feature within the wall and being configured to confine energy within a cavity, wherein at least a portion of the fluid flow path extends through the cavity.

The fluid conduit may be configured to provide energy to a fluid present in or flowing through the fluid conduit to affect one or more properties of the fluid.

The fluid conduit may be configured to concentrate and/or focus energy on a fluid present in or flowing through the fluid conduit.

The fluid conduit may be configured to impart a change in the fluid and/or permit a change in the fluid to be measured.

The fluid conduit may be configured to heat or agitate a fluid or to encourage separation of components and/or phases of a fluid present in or flowing through the fluid conduit.

The fluid conduit may be configured for sensing a property of a fluid present in or flowing through the fluid conduit or for use in sensing a property of a fluid present in or flowing through the fluid conduit.

The fluid conduit may comprise or be associated with a sensor arrangement for sensing or for use in sensing a property of a fluid present in or flowing through the fluid conduit.

The fluid conduit may comprise or be associated with one or more sensors for sensing a property of a fluid present in or flowing through the fluid conduit or for use in sensing a property of a fluid present in or flowing through the fluid conduit.

The fluid conduit may be used to identify a fluid present in or flowing through the fluid flow path.

The fluid conduit may be used to determine a composition of a fluid present in or flowing through the fluid flow path.

The fluid conduit may permit unrestricted flow of fluid along the fluid flow path. This may serve to prevent a pressure change such as a drop within the fluid flow path that would otherwise occur if the fluid conduit were to comprise one or more projections extending into the fluid flow path. The fluid conduit may also permit the unrestricted movement of tools, equipment or the like along the fluid flow path. The fluid conduit may facilitate pigging operations. Such operations may, for example, be used to survey an interior of the fluid conduit, clean an interior of the fluid conduit, remove hydrate build-up from an interior of the fluid conduit and the like.

Such a fluid conduit may ensure that the confinement feature is not exposed to the fluid so as to avoid damage or contamination of the confinement feature by the fluid. For example, the fluid conduit may ensure that contaminants, particulate matter, or deposits such as hydrates or the like do not come into contact with or adhere to the confinement feature. The fluid conduit may ensure that the effects of the fluid on the confinement feature are eliminated or at least partially suppressed. For example, the fluid conduit may eliminate or at least partially suppress the effects of fluid pressure from acting on the confinement feature and/or may eliminate or reduce heat transfer between the fluid and the confinement feature.

The confinement feature may be configured to confine electromagnetic energy. For example, the confinement feature may be configured to confine an electromagnetic field.

The confinement feature may be configured to confine electric and/or magnetic energy.

The confinement feature may be configured to confine an electric field.

The confinement feature may be configured to confine a magnetic field.

The confinement feature may be configured to confine electromagnetic energy generated as a result of nuclear magnetic resonance (NMR) in a fluid present in or flowing through the fluid flow path.

The confinement feature may be configured to confine radio frequency electromagnetic energy. For example, the confinement feature may be configured to confine a radio frequency electromagnetic field.

The confinement feature may be configured to confine ultraviolet, optical, mm-wave and/or microwave frequency electromagnetic energy. For example, the confinement feature may be configured to confine an ultraviolet frequency, an optical frequency, a mm-wave frequency and/or a microwave frequency electromagnetic field.

The confinement feature may be configured to confine acoustic energy. For example, the confinement feature may be configured to confine an acoustic field.

The confinement feature may be configured to confine a radioactive emission. For example, the confinement feature may be configured to confine alpha particles, beta particles and/or gamma rays or the like.

The confinement feature may be configured to partially confine energy within the cavity.

The confinement feature may be configured to substantially confine energy within the cavity.

The confinement feature may be configured to wholly confine the energy within the cavity.

The confinement feature may be configured to concentrate and/or focus energy.

The confinement feature may comprise a reflector or a mirror or the like.

The confinement feature may at least partially define the cavity.

The confinement feature may at least partially surround the fluid flow path.

The confinement feature may be arranged generally laterally to an axis of the fluid flow path.

The confinement feature may extend along a portion of an axis of the fluid flow path.

The confinement feature may comprise a metal. For example, the confinement feature may comprise steel, aluminium, copper or the like. The confinement feature may comprise a cavity member which is separately formed from the wall.

The cavity member may be enclosed or embedded within the wall.

Embedding a cavity member within the wall may serve to provide mechanical support for the cavity member and/or the wall. In addition, embedding a cavity member within the wall may provide alignment between one or more features of the cavity member and one or more features of the wall.

The cavity member may comprise an outer portion that defines an interior region through which the fluid flow path extends.

The cavity member may comprise a projecting portion that extends from the outer portion of the cavity member into the interior region towards the fluid flow path.

The projecting portion of the cavity member may comprise a base portion which is connected to the outer portion of the cavity member and a distal end portion which is distal from the outer portion of the cavity member. The distal end portion may be enlarged relative to the base portion. Such an arrangement of the projecting portion may provide an enhancement of electric field strength in the vicinity of the base and distal end portions.

The projecting portion of the cavity member may be formed as a coil. Such an arrangement of the projecting portion may provide an enhancement of magnetic field strength within the coil.

The cavity member may comprise a metal. For example, the cavity member may comprise steel, aluminium, copper or the like.

The cavity member may comprise a cavity member wall which defines the cavity.

The cavity member wall may be solid.

The cavity member wall may have one or more hollow regions formed therein.

The cavity member may comprise a cavity member inner wall and a cavity member outer wall, wherein the cavity member inner wall defines the cavity and the cavity member inner and outer walls define a hollow region therebetween.

The confinement feature may be formed within the wall of the fluid conduit. The confinement feature may comprise a hollow region of the wall of the fluid conduit.

The confinement feature may comprise and/or define a waveguide. For example, the confinement feature may comprise and/or define a waveguide for guiding energy to and/or from the cavity.

The cavity may be a resonant cavity.

The cavity may be configured to be resonant at a predetermined frequency or over a predetermined range or frequencies.

The cavity may be configured to be resonant at a predetermined frequency associated with a region of the electromagnetic spectrum such as a radio, microwave, mm-wave, infrared, optical, ultraviolet and/or gamma ray frequency or the like.

The cavity may be configured to be resonant at a predetermined acoustic frequency.

The cavity may be configured to be resonant over a predetermined range of frequencies associated with a region of the electromagnetic spectrum such as a range of radio, microwave, mm-wave, infrared, optical, ultraviolet and/or gamma ray frequencies or the like.

The cavity may be configured to be resonant over a predetermined range of acoustic frequencies.

The cavity may be configured to be resonant at a frequency or range of frequencies characteristic of a particular fluid present in or flowing through the fluid flow path. This may serve to impart a greater amount of energy to the fluid present in or flowing through the fluid flow path. This may increase the sensitivity with which a property of the fluid may be determined from measurements of one or more properties associated with resonance in the cavity.

The cavity may be configured to be resonant at a predetermined frequency or over a predetermined range or frequencies characteristic of a target component such as a contaminant within the fluid. For example, the cavity may be configured to be resonant at a predetermined frequency or over a predetermined range or frequencies characteristic of a concentration or a range of concentrations of a target component such as contaminant within the fluid.

The fluid conduit may comprise a coupling element such as a coupler, antenna or the like for coupling energy to and/or from the cavity.

The fluid conduit may comprise a coupling element for coupling electromagnetic energy to and/or from the cavity.

The fluid conduit may comprise a coupling element for coupling electromagnetic energy to and/or from an electric field. For example, the fluid conduit may comprise a stub coupler.

The fluid conduit may comprise a coupling element for coupling electromagnetic energy to and/or from a magnetic field. For example, the fluid conduit may comprise an inductance coupler such as a loop coupler.

The fluid conduit may comprise a coupling element for coupling electromagnetic energy to and/or from an optical field.

The fluid conduit may comprise a coupling element for coupling acoustic energy to and/or from an acoustic field.

The fluid conduit may comprise a coupling element for coupling a radioactive emission to and/or from the cavity.

The coupling element may be recessed, enclosed or embedded within the wall. Such an arrangement may ensure that the coupling element does not extend into the fluid flow. Such an arrangement may, therefore, permit unrestricted flow of fluid along the fluid flow path and prevent any pressure drop within the fluid flow path that would otherwise occur if the coupling element were to extend into the fluid flow path. Such an arrangement may also permit the unrestricted movement of tools, equipment or the like along the fluid flow path. Such an arrangement may facilitate pigging operations. Such operations may, for example, be used to survey an interior of the fluid conduit, clean an interior of the fluid conduit, remove hydrate build-up from an interior of the fluid conduit and the like.

Embedding or enclosing the coupling element within the wall may ensure that the coupling element is not exposed to the fluid so as to avoid damage or contamination of the coupling element by the fluid. For example, such an arrangement may ensure that the coupling element does not become clogged with particulate matter that may be entrained within the fluid. Such an arrangement may ensure that the effects of the fluid on the coupling element are eliminated or at least partially suppressed. For example, such an arrangement may prevent or at least partially reduce the effects of fluid pressure from acting on the coupling element and/or may eliminate or at least partially reduce heat transfer between the fluid and the coupling element.

Embedding the coupling element within the wall may serve to provide mechanical support for the coupling element and/or the wall. In addition, embedding the coupling element within the wall may provide alignment between one or more features of the coupling element and one or more features of the wall.

The coupling element may extend at least partially through a cavity member. For example, the coupling element may extend at least partially through a projecting portion of the cavity member that extends from an outer portion of the cavity member towards the fluid flow path.

The fluid conduit may comprise a further coupling element for coupling energy to and/or from the cavity.

The wall may be configured to transmit energy between the confinement feature and the fluid flow path.

The wall may be configured to have a negligible or relatively insignificant effect on the transmission of energy between the confinement feature and the fluid flow path.

The wall may be configured, in particular, to minimise disruption, distortion and/or absorption of an energy field extending between the confinement feature and the fluid flow path. The wall may be configured to have a negligible or relatively insignificant effect on measurements of one or more properties associated with resonance in the cavity.

The wall may be formed from a material having an electrical permittivity value which is less than a threshold electrical permittivity value. The wall may be formed from a material having a complex electrical permittivity having real and imaginary components, wherein the real component is less than a threshold real electrical permittivity component value and/or the imaginary component is less than a threshold imaginary electrical permittivity component value.

The wall may be formed from a material having a magnetic susceptibility value which is less than a threshold magnetic susceptibility value. The wall may be formed from a material having a complex magnetic susceptibility having real and imaginary components, wherein the real component is less than a threshold real magnetic susceptibility component value and/or the imaginary component is less than a threshold imaginary magnetic susceptibility component value.

The wall may be formed from a material having a refractive index value which is less than a threshold refractive index value. The wall may be formed from a material having an optical absorption parameter value which is less than a threshold optical absorption parameter value.

The wall may be formed from a material having a density which is less than a threshold density. The wall may be formed from a material having an acoustic absorption parameter value which is less than a threshold acoustic absorption parameter value.

The wall may be configured to affect an energy field in the cavity in a known or quantifiable manner. Such a wall may allow one or more properties of a fluid present within or flowing through the fluid flow path to be deconvolved from measurements of one or more properties of the energy field.

The wall may be substantially homogeneous at a microscopic level.

The wall may, in particular, be configured to have a known or quantifiable effect on measurements of one or more properties associated with resonance in the cavity. This may allow one or more properties of a fluid present within or flowing through the fluid flow path to be deconvolved from measurements of one or more properties associated with resonance in the cavity.

The wall may, in particular, be configured to affect an electric and/or a magnetic field in the cavity in a known or quantifiable manner to allow one or more properties of a fluid present within or flowing through the fluid flow path to be deconvolved from measurements of one or more properties of the electric and/or a magnetic field such as one or more properties associated with resonance in the cavity.

The wall may comprise a non-conventional pipe material such as a non-metallic material. For example, the wall may comprise a polymer material, a thermoplastic material, a thermoset material, a polyaryl ether ketone, a polyaryl ketone, a polyether ketone (PEK), a polyether ether ketone (PEEK), a polycarbonate, a polymeric resin, an epoxy resin and/or the like. Forming the wall from one or more non-conventional pipe materials may provide various advantages for imparting energy to a fluid present in or flowing through the fluid flow path. For example, a wall formed from one or more non-conventional pipe materials may have a negligible or relatively insignificant effect on the transmission of energy therethrough and/or may be homogeneous at a microscopic level so as to affect an energy field in the cavity in a known or quantifiable manner. In addition, such a wall may be less susceptible to surface degradation, deterioration and/or corrosion and/or to the deposition of substances such as hydrates or the like thereon. Consequently such a wall may be less susceptible to degradation in the sensitivity of any measurements performed on a fluid or fluids present in or flowing through the fluid flow path compared with a wall formed from a conventional pipe material such as a metallic material. Furthermore, a wall formed from one or more non-conventional pipe materials may be less susceptible to degradation caused by any incidence of radioactive emission on the wall compared with a wall formed from a conventional pipe material such as steel.

The wall may comprise a conventional pipe material such as a metal or the like. For example, the wall may comprise steel, aluminium, copper or the like.

The wall may be configured to have a different effect on the transmission of energy therethrough to the effect provided by a fluid present in or flowing through the fluid conduit.

The wall may comprise an outer region formed from a first material and an inner region formed from a second material different from the first material, wherein the confinement feature is arranged within the inner region or is arranged within the wall between the inner and outer regions.

The wall may comprise an outer region formed from a conventional pipe material such as a metal or the like and an inner region formed from a polymer material, a thermoplastic material, a thermoset material, a polyaryl ether ketone, a polyaryl ketone, a polyether ketone (PEK), a polyether ether ketone (PEEK), a polycarbonate, a polymeric resin, an epoxy resin and/or the like.

The wall may comprise an inert region extending between the confinement feature and the fluid flow path, wherein the inert region is configured to have a negligible or relatively insignificant effect on the transmission of energy therethrough. The inert region may be configured, in particular, to minimise disruption, distortion and/or absorption of an energy field extending therethrough. The inert region may be configured to have a negligible or relatively insignificant effect on measurements of one or more properties associated with resonance in the cavity.

The inert region may comprise a material or materials which are substantially inert with respect to transmission of energy therethrough.

The inert region may be formed from a material having an electrical permittivity value which is less than a threshold electrical permittivity value. The inert region may be formed from a material having a complex electrical permittivity having real and imaginary components, wherein the real component is less than a threshold real electrical permittivity component value and/or the imaginary component is less than a threshold imaginary electrical permittivity component value.

The inert region may be formed from a material having a magnetic susceptibility value which is less than a threshold magnetic susceptibility value. The inert region may be formed from a material having a complex magnetic susceptibility having real and imaginary components, wherein the real component is less than a threshold real magnetic susceptibility component value and/or the imaginary component is less than a threshold imaginary magnetic susceptibility component value.

The inert region may be formed from a material having a refractive index value which is less than a threshold refractive index value. The inert region may be formed from a material having an optical absorption parameter value which is less than a threshold optical absorption parameter value.

The inert region may be formed from a material having a density which is less than a threshold density. The inert region may be formed from a material having an acoustic absorption parameter value which is less than a threshold acoustic absorption parameter value.

The inert region may define the fluid flow path.

The wall may comprise a homogeneous region extending between the confinement feature and the fluid flow path, wherein the homogeneous region is substantially homogeneous at a microscopic level.

The homogeneous region may be configured to affect an energy field in the cavity in a known or quantifiable manner. Such a homogeneous region may allow one or more properties of a fluid present within or flowing through the fluid flow path to be deconvolved from measurements of one or more properties of the energy field.

The homogeneous region may, in particular, be configured to have a known or quantifiable effect on measurements of one or more properties associated with resonance in the cavity. This may allow one or more properties of a fluid present within or flowing through the fluid flow path to be deconvolved from measurements of one or more properties associated with resonance in the cavity.

The homogeneous region may define the fluid flow path.

The homogeneous region may, in particular, be configured to affect an electric and/or a magnetic field in the cavity in a known or quantifiable manner to allow one or more properties of a fluid present within or flowing through the fluid flow path to be deconvolved from measurements of one or more properties of the electric and/or a magnetic field such as one or more properties associated with resonance in the cavity.

The homogeneous region may be configured to have a negligible or relatively insignificant effect on the transmission of energy therethrough.

The wall may comprise a composite material formed of at least a matrix and one or more reinforcing elements embedded within the matrix.

The matrix may define a monolithic structure. That is, the structure of the matrix material may be continuous.

The wall may comprise a composite material formed of at least a matrix and a plurality of reinforcing elements embedded within the matrix. The distribution or concentration of the reinforcing elements may vary within the matrix.

The wall may comprise a matrix and a plurality of reinforcing elements embedded within the matrix, wherein the concentration of the reinforcing elements within the wall varies radially, circumferentially and/or axially with respect to an axis of the fluid conduit.

The wall may comprise a matrix and a plurality of reinforcing elements embedded within the matrix, wherein the concentration of the reinforcing elements increases with distance from the fluid flow path.

The wall may comprise a matrix and a plurality of reinforcing elements embedded within the matrix, wherein a region of the wall adjacent to the fluid flow path is substantially devoid of reinforcing elements.

The wall may comprise a matrix and a plurality of reinforcing elements embedded within the matrix, wherein a region of the wall between the confinement feature and the fluid flow path is substantially devoid of reinforcing elements. Such a distribution of reinforcing elements may define a region of the wall between the confinement feature and the fluid flow path which has a negligible or relatively insignificant effect on an energy field extending therethrough. Such a distribution of reinforcing elements may define a region of the wall between the confinement feature and the fluid flow path which is substantially homogeneous at a microscopic level.

The matrix may comprise a polymer material.

The matrix may comprise a thermoplastic material.

The matrix may comprise a thermoset material.

The matrix may comprise a polyaryl ether ketone, a polyaryl ketone, a polyether ketone (PEK), a polyether ether ketone (PEEK), a polycarbonate and/or the like. The matrix may comprise a polymeric resin, such as an epoxy resin or the like.

The reinforcing elements may comprise continuous or elongate elements. The reinforcing elements may comprise polymeric fibres, for example aramid fibres. The reinforcing elements may comprise non-polymeric fibres, for example carbon, glass, basalt fibres and/or the like. The reinforcing elements may comprise fibres, strands, filaments, nanotubes or the like. The reinforcing elements may comprise discontinuous elements.

The matrix and the reinforcing elements may comprise similar or identical materials. For example, the reinforcing elements may comprise the same material as the matrix, albeit in a fibrous, drawn, elongate form or the like.

The fluid conduit may comprise an arrangement for generating energy.

The fluid conduit may comprise an arrangement for generating an energy field in the cavity.

The fluid conduit may comprise a positive feedback arrangement.

The fluid conduit may comprise an arrangement for generating an electromagnetic field.

The fluid conduit may comprise a positive feedback arrangement for providing positive feedback of electromagnetic energy.

The positive feedback arrangement may comprise two terminals which are both coupled to the cavity.

One terminal of the positive feedback arrangement may be coupled to the coupling element and the other terminal of the positive feedback arrangement may be coupled to either the confinement feature or to a further coupling element for coupling energy to and/or from the cavity.

The positive feedback arrangement may comprise a gain element, amplifier, negative resistance or the like.

The positive feedback arrangement may comprise a limiter. The limiter may be coupled in series with an amplifier.

The positive feedback arrangement may comprise an RF amplifier, a microwave amplifier or a mm-wave amplifier or the like.

The positive feedback arrangement may comprise an optical gain medium.

The positive feedback arrangement may comprise a transducer such as an acoustic transducer.

The fluid conduit may comprise an oscillator defined by the cavity and the positive feedback arrangement. For example, the fluid conduit may comprise a Robinson oscillator.

The fluid conduit may comprise an output arranged to provide a signal that varies according to a value of a resonant frequency and/or a loss of the oscillator.

The fluid conduit may comprise an output arranged to provide a signal that varies according to a value of a resonant frequency and/or an electromagnetic loss of the oscillator.

The fluid conduit may comprise or be associated with a processor arrangement which is configured to extract a value for a resonant frequency of the oscillator and/or extract a value for an electromagnetic loss of the oscillator from a signal that varies according to a value of a resonant frequency and/or an electromagnetic loss of the oscillator.

The fluid conduit may comprise or be associated with a demodulator, a mixer and/or the like for use in providing a signal which varies with a resonant frequency of the oscillator and/or a signal which varies with a loss of the oscillator.

Knowledge of both the resonant frequency and loss may provide an indication of whether a property of a fluid present in or flowing through a cavity is within a prescribed parameter range regardless of the quantity of fluid present in or flowing through the cavity. Knowledge of both the resonant frequency and loss may provide an indication of the quantity of fluid present in or flowing through the cavity regardless of whether a property of a fluid present in or flowing through the cavity is known to be within a prescribed parameter range.

Measurements of the resonant frequency and loss may, therefore, be used to identify the fluid present in or flowing through the fluid flow path.

Measurements of the resonant frequency and loss may be used to determine the composition of a fluid present in or flowing through the fluid flow path.

Measurements of the resonant frequency and loss may be used to determine a gas and/or liquid proportion of the fluid.

Measurements of the resonant frequency and loss may be used to determine a proportion of water and a proportion of a hydrocarbon fluid within the fluid.

Measurements of the resonant frequency and loss may be used to determine a type or property of crude oil or water present in or flowing through the fluid flow path.

Measurements of the resonant frequency and loss may be used to determine the proportion of oil such as crude oil, methanol, methane, natural gas or the like within the fluid.

Measurements of the resonant frequency and loss may be used to determine acid content of oil present in or flowing through the fluid flow path.

Measurements of the resonant frequency and loss may be used to determine the salinity of water present in or flowing through the fluid flow path.

Measurements of the resonant frequency and loss may be used to determine one or more physical characteristics of the fluid such as flow rate, viscosity, temperature, pressure and the like.

Such an arrangement may, therefore, permit a concentration of a target component such as a contaminant within the fluid to be determined from measurements of the resonant frequency and loss irrespective of the fluid flow rate. Such an arrangement may permit a fluid flow rate to be determined from measurements of the resonant frequency and loss irrespective of the concentration of a target component such as a contaminant within the fluid.

The fluid conduit may comprise an energy source.

The energy source may be coupled to at least one of the coupling element, the further coupling element and the confinement feature.

The fluid conduit may comprise a source of electromagnetic energy. The source of electromagnetic energy may be coupled to at least one of the coupling element, the further coupling element and the confinement feature.

The fluid conduit may comprise a source of acoustic energy.

The fluid conduit may comprise a radioactive source.

The fluid conduit may comprise a tuning member. The tuning member may be adjustable so as to vary a resonant frequency or a resonant frequency range of the cavity. For example, the tuning member may be movable within the cavity.

The fluid conduit may comprise a sensor configured to measure temperature. For example, the fluid conduit may comprise a resistance temperature detector (RTD), a thermistor, a thermocouple of the like. The temperature sensor may be recessed, enclosed or embedded within the wall of the fluid conduit. In use, such a temperature sensor may assist in resolving a fluid or composition of a fluid present in or flowing through the fluid flow path.

The fluid conduit may comprise a sensor configured to measure a pressure of a fluid present in or flowing through the fluid flow path. For example, the fluid conduit may comprise a strain gauge, a piezoelectric sensor, a capacitive, optical, or magnetic pressure sensor, a pressure gauge or a pressure sensor of any other kind. The pressure sensor may be recessed, enclosed or embedded within the wall of the fluid conduit. In use, such a pressure sensor may assist in resolving a fluid or composition of a fluid present in or flowing through the fluid flow path.

The pressure sensor may be configured to measure a pressure of a fluid in the fluid flow path directly or to measure a pressure of a fluid in the fluid flow path indirectly by measuring the effects of fluid pressure on the wall of the fluid conduit.

The fluid conduit may comprise a sensor configured to sense flow rate within the fluid flow path. For example, the fluid conduit may comprise a fluid flow control feature configured to affect fluid flow in the fluid flow path and one or more fluid flow sensors configured to sense a change induced in the fluid flow by the fluid flow control feature.

The one or more fluid flow sensors may be configured to sense one or more fluid pressures in the fluid flow path.

The fluid flow control feature may induce a temporal or a spatial change in the fluid flow.

The fluid flow control feature may comprise a restriction such as a Venturi in the fluid flow path. The one or more fluid flow sensors may be configured to sense fluid pressure upstream, downstream and/or within the restriction in the fluid flow path.

The fluid conduit may comprise a vortex shedding flow rate sensor.

The fluid conduit may comprise a plurality of confinement features. For example, the fluid conduit may comprise a plurality of confinement features within the wall.

Each of the plurality of confinement features may confine energy within a corresponding cavity, wherein at least a portion of the fluid flow path extends through each cavity. For example, a different portion of the fluid flow path may extend through each cavity.

Each of the plurality of confinement features may confine energy within a corresponding cavity, wherein one or more of the cavities may be configured to be resonant.

Each of the plurality of confinement features may confine energy within a corresponding cavity, wherein one or more of the cavities may be resonant at a respective frequency or over a respective range of frequencies. For example, each cavity may be configured to be resonant at a different frequency or over a different range of frequencies.

Each of the plurality of confinement features may be arranged generally laterally to an axis of the fluid flow path.

Each of the plurality of confinement features may extend along a portion of an axis of the fluid flow path.

Each of the plurality of confinement features may have a different spatial arrangement.

Each of the plurality of confinement features may be separated axially along an axis of the fluid flow path.

Each of the plurality of confinement features may have a different angular orientation about an axis of the fluid flow path.

The fluid conduit may comprise two confinement features, each confinement feature being arranged generally laterally to an axis of the fluid flow path, each confinement feature being separated axially along an axis of the fluid flow path and each confinement feature having an angular separation of 90° about the axis of the fluid flow path relative to the other confinement feature.

The fluid conduit may comprise three confinement features, each confinement feature being arranged generally laterally to an axis of the fluid flow path, each confinement feature being separated axially along an axis of the fluid flow path and each confinement feature having an angular separation of 120° about the axis of the fluid flow path relative to the other confinement features.

The wall of the fluid conduit may comprise axial end portions formed from a first material and a axial middle portion comprising an outer region formed from the first material and an inner region formed from a second material different from the first material, wherein the confinement feature is arranged within the inner region of the axial middle portion or is arranged between the inner and outer regions of the axial middle portion. The axial end portions may each comprise a flange formed from the first material for connection to a respective pipe length. Such an arrangement may permit the fluid conduit to be connected via the flanges of the axial end portions to a flange of a respective standard pipe, whilst still accommodating the confinement feature within the axial middle portion of the wall of the fluid conduit.

The fluid conduit may be configured for connection to one or more lengths of pipe.

The fluid conduit may be configured for connecting two lengths of pipe.

The fluid conduit may comprise first and second ends, each of the first and second ends being configured for connection to a respective pipe length.

The fluid conduit may comprise a first flange located at a first end and a second flange located at a second end, each of the first and second flanges being configured for connection to a respective pipe length.

The fluid conduit may comprise one or more through holes that extend along a length of the fluid conduit, the through holes being configured for attachment of the fluid conduit to a respective pipe length located at either end of the fluid conduit via fasteners or the like which extend through the through holes.

A further aspect of the present invention relates to a fluid conduit, comprising:

a wall defining a fluid flow path and comprising a composite material formed of at least a matrix and one or more reinforcing elements embedded within the matrix; and a component at least partially embedded within the wall and configured to transmit energy to and/or receive energy from the flow path, wherein a region of the wall between the component and the fluid flow path is substantially devoid of reinforcing elements to define a transmission path for energy between the fluid flow path and component.

The matrix material may define a monolithic structure. In such an arrangement the matrix material may extend continuously between that portion of the wall which includes reinforcing elements and that portion of the wall which is substantially devoid of reinforcing elements.

The component may be configured for use in determining a property of a fluid contained within, or flowing through the flow path defined by the conduit. For example, the component may receive or detect energy from the fluid conduit, wherein a feature of said energy may be used to determine a property of the fluid contained within or flowing through the flow path.

The component may be configured for use in transmitting energy into a fluid contained within or flowing through the flow path. For example, the energy transmitted may be selected to affect a property of the fluid, for example to heat the fluid or the like. The transmitted energy may be detected and used for determining a property of the fluid. The energy may be detected by the same component. The energy may be detected by a different component. The different component may also be at least partially embedded within the wall of the fluid conduit.

The component may comprise at least one of a transducer, a sensor, a receiver, a transmitter, a transceiver, an antenna and confinement feature.

The fluid conduit may comprise multiple components at least partially embedded within the wall.

Another aspect of the present invention relates to a pipeline for a fluid comprising one or more lengths of pipe and a fluid conduit according to any other aspect.

The pipeline may comprise a plurality of pipe lengths.

The pipeline may comprise a plurality of fluid conduits.

Adjacent pipe lengths may be joined by a fluid conduit.

Each fluid conduit may be configured to identify a different fluid present in or flowing through the fluid flow path.

Each fluid conduit may be configured to identify a different fluid component present in or flowing through the fluid flow path.

Each fluid conduit may be configured to be resonant at a different predetermined frequency or over a different predetermined range or frequencies.

It should be understood that the any feature described in relation to one aspect of the present invention may apply alone or in any combination in relation to any other aspect.

BRIEF DESCRIPTION OF THE DRAWINGS

The present invention will now be described by way of non-limiting example only with reference to the following drawings of which.

DETAILED DESCRIPTION OF THE DRAWINGS

Figure 1A:
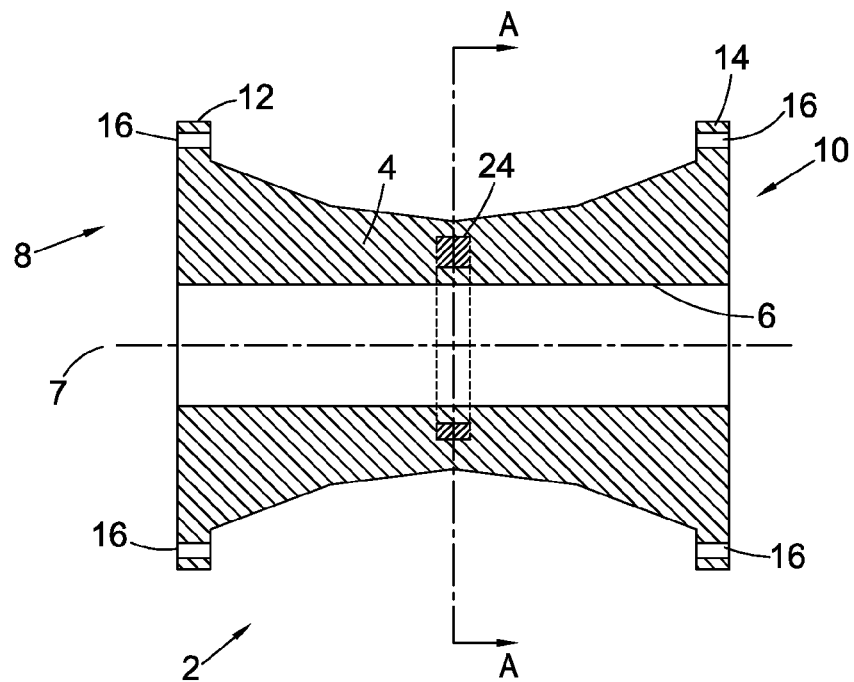
FIG. 1(a) is a longitudinal cross-section of a fluid conduit constituting a first embodiment of the present invention.
Figure 1B:
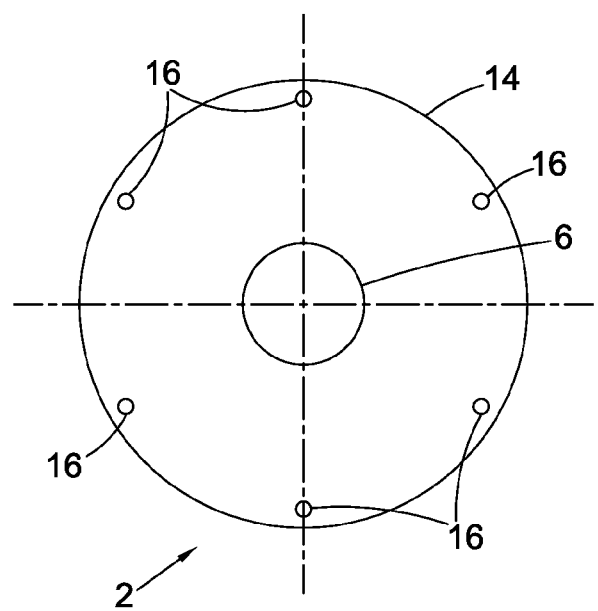
FIG. 1(b) is an end elevation of the fluid conduit of FIG. 1(a)

Referring initially to FIGS. 1(a) and 1(b) there is shown a fluid conduit generally designated 2 having a wall 4 which defines a bore 6 for fluid flow. The bore 6 is arranged along an axis 7 of the fluid conduit 2. The bore 6 extends between a first end 8 of the fluid conduit 2 to a second end 10 of the fluid conduit 2. The fluid conduit 2 comprises a first flange portion 12 formed at the first end 8 and a second flange portion 14 formed at the second end 10. The flange portions 12, 14 comprises clearance holes 16 to permit connection of each flange portion 12, 14 to a corresponding flange portion at an end of a length of pipe or a further fluid conduit (not shown) using fasteners such as bolts (not shown). Embedded within the wall 4 is a confinement feature for an electromagnetic field in the form of a steel cavity member 24 which extends axially part-way along the length of the fluid conduit 2 between the first and second ends 8, 10.

Figure 2:
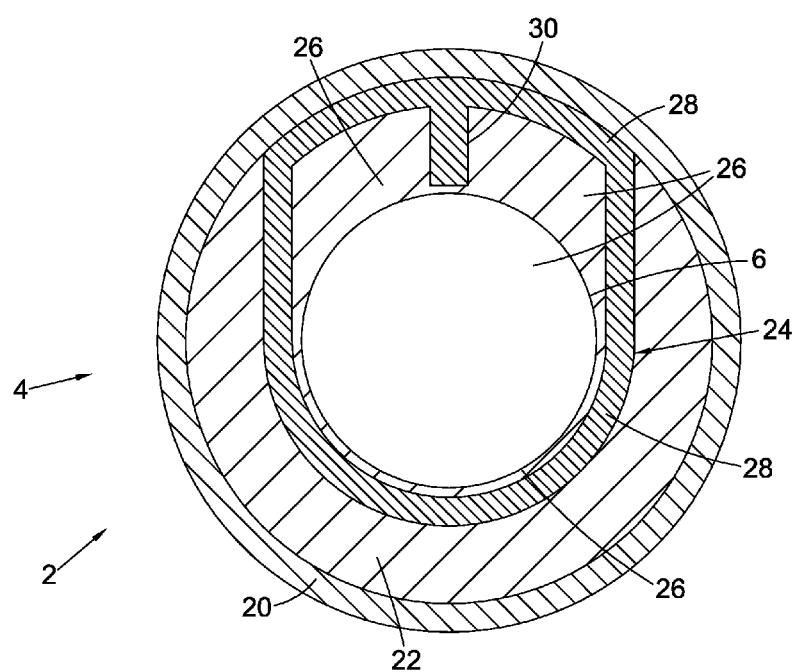
FIG. 2 is a lateral cross-section on AA of the fluid conduit of FIG. 1(a)

As shown in cross-section in FIG. 2, the wall 4 comprises a composite region 20 and a homogeneous region 22 which defines the bore 6. The composite region 20 comprises a matrix of a polyether ether ketone (PEEK) and a plurality of reinforcing elements in the form of carbon fibres (not shown explicitly) embedded within the PEEK. The homogeneous region 22 comprises PEEK and is devoid or at least substantially devoid of any reinforcing elements at a microscopic level. The PEEK material of regions 20 and 22 defines a monolithic structure and extends continuously between said regions. Accordingly, it may be considered that the entire wall 4 is of a composite construction of a matrix and reinforcing elements, wherein inner region 22 is substantially devoid of reinforcing elements.

The cavity member 24 is fully embedded within the homogeneous region 22 of the wall 4 of the fluid conduit 2 so as to seal the cavity member 24 with respect to the bore 6 and prevent exposure of the cavity member 24 to any fluid present in or flowing through the bore 6. The cavity member 24 is configured to confine an electromagnetic field within a cavity 26 which contains a portion of the bore 6 and a portion of the homogeneous region 22 between the bore 6 and the cavity member 24. The PEEK material constituting the homogeneous region 22 is relatively inert with respect to electromagnetic fields at RF frequencies. More explicitly, PEEK has relatively low real and imaginary dielectric permittivity components and relatively low real and imaginary magnetic susceptibility components so as to minimise any distortion of the electromagnetic field between the cavity member 24 and the bore 6.

Figure 3:
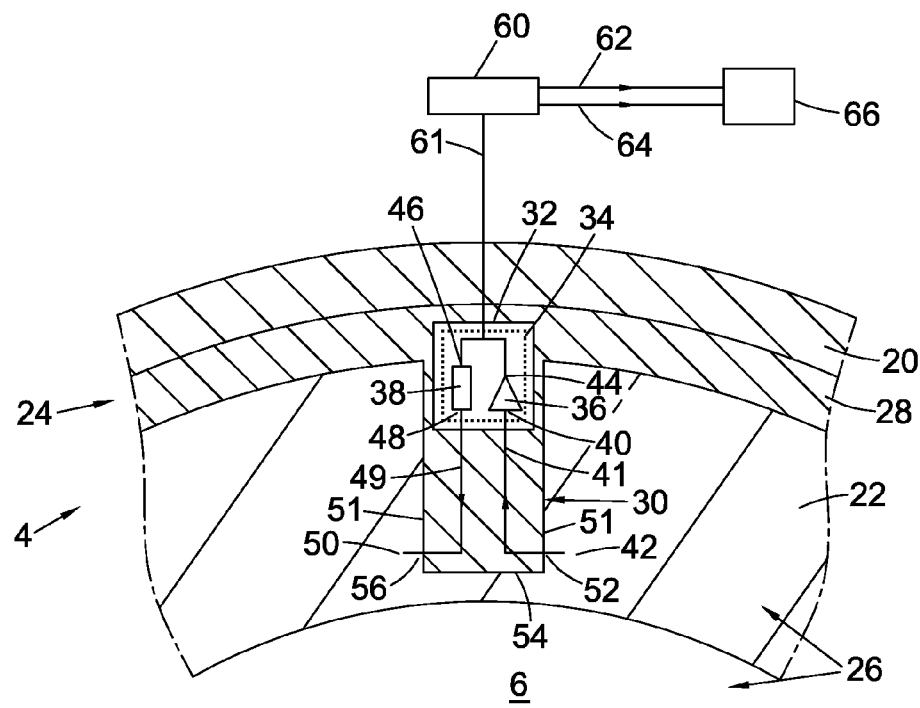
FIG. 3 shows a field coupling region of the lateral cross-section of FIG. 2.

As shown in more detail in FIG. 3, the cavity member 24 comprises an outer portion 28 and a generally cylindrical projecting portion 30 which extends radially inwardly from the outer portion 28 into the cavity 26. The cavity member 24 further comprises a hollow portion 32 in the vicinity of the projecting portion 30. The hollow portion 32 houses a positive feedback arrangement designated 34 comprising an RF amplifier 36 electrically coupled in series with a limiter 38. An input terminal 40 of the RF amplifier 36 is coupled via a waveguide 41 to an input stub coupler 42 for coupling energy from an electric field component of an electromagnetic field within the cavity 26. An output terminal 44 of the RF amplifier 26 is coupled to an input terminal 46 of the limiter 38. An output terminal 48 of the limiter 38 is coupled via a waveguide 49 to an output stub coupler 50 for coupling energy to an electric field component of an electromagnetic field within the cavity 26. The input and output stub couplers 42, 50 and the waveguides 41, 49 are electrically insulated from the cavity member 24.

The input stub coupler 42 extends generally laterally from a cylindrical surface 51 of the projecting portion 30 at a position 52 which is adjacent to a distal end 54 of the projecting portion 30. The output stub coupler 50 extends generally laterally from the cylindrical surface 51 from a position 56 adjacent to the distal end 54. The position 56 from which the output stub coupler 50 extends is diametrically opposite to the position 52 from which the input stub coupler 42 extends. The direction in which the output stub coupler 50 extends is generally opposite to the direction in which the input stub coupler 42 extends.

Together the RF amplifier 36, the limiter 38, the input and output stub couplers 42, 50 and the cavity 26, constitute a Robinson oscillator. The output terminal 44 of the RF amplifier 26 and the input terminal of the limiter 38 are coupled to a demodulator 60 located externally of the fluid conduit 2 via an insulated waveguide 61. The demodulator 60 is configured to provide an output signal 62 representative of a resonant frequency of the oscillator and an output signal 64 representative of an electromagnetic loss of the oscillator as described in more detail below. The demodulator 60 is configured for communication of the output signals 62, 64 to a processor 66.

In use, power is provided to the amplifier 36 which acts, together with the limiter 38, to generate an electromagnetic field in the cavity 26 having a resonant frequency which depends on the configuration and contents of the cavity 26. The cavity 26 is configured such that the electromagnetic field extends into the bore 6 such that a resonant frequency of the cavity 26 depends on the properties of any fluid which is present in or flowing through the bore 6. The processor 66 receives the output signals 62 and 64 and uses the output signals 62 and 64 to identify the fluid present in or flowing through the bore 6 according to the Robinson principle as set forth in WO2009/118569 which is incorporated herein by reference in its entirety.

The fluid conduit 2 may be configured to determine the composition of a fluid present in or flowing through the bore 6. For example, the fluid conduit 2 may be configured to determine a gas and/or liquid proportion of the fluid present in or flowing through the bore 6. The fluid conduit 2 may be configured to determine a water component and/or a hydrocarbon fluid component such as a crude oil component within the fluid present in or flowing through the bore 6.

Figure 4:
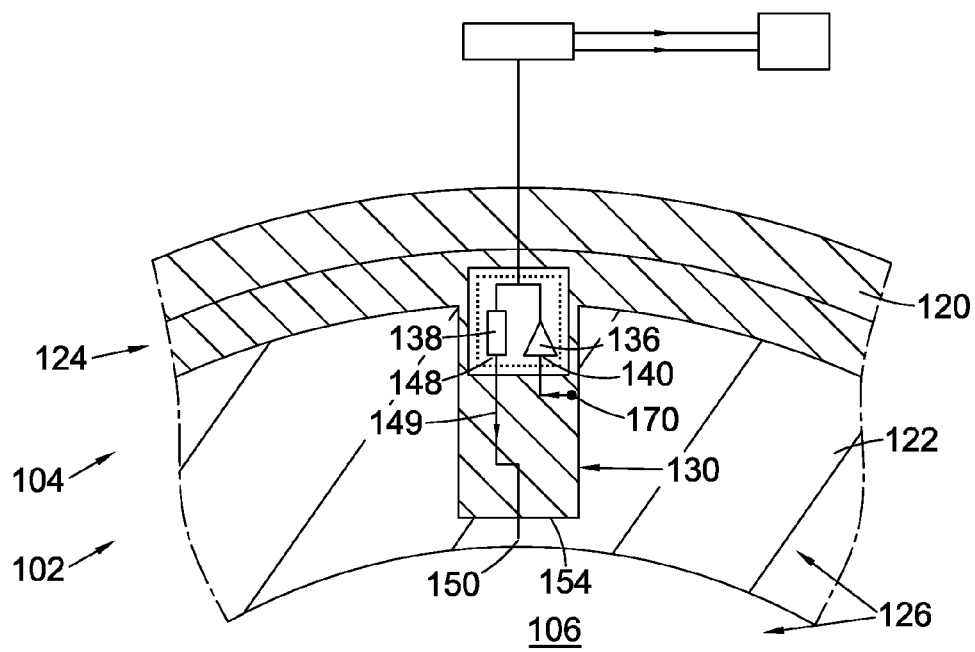
FIG. 4 is a detailed lateral cross-section of a field coupling region of a wall of a second fluid conduit embodiment.

FIG. 4 shows a detailed lateral cross-section of a field coupling region of a wall 104 of a fluid conduit generally designated 102 constituting a second embodiment of the present invention. The fluid conduit 102 of FIG. 4 shares many like features with the fluid conduit 2 of the first embodiment already described with reference to FIGS. 1-3. As such, the features of the fluid conduit 102 are identified with the same reference numerals used for the corresponding features of the fluid conduit 2 but incremented by "100". Like the fluid conduit 2 of FIGS. 1-3, the fluid conduit 102 of FIG. 4 comprises a wall 104 having a homogeneous region 122 (for example, a matrix material devoid of reinforcing fibres) which defines a bore 106 for fluid flow. The fluid conduit 102 also comprises a cavity member 124 embedded in the homogeneous region 122 so as to define a cavity 126 for an electromagnetic field. The fluid conduit 102 of FIG. 4 differs from the fluid conduit 2 of FIGS. 1-3 only in the coupling arrangement between a positive feedback arrangement 134 and an electric field in the cavity 126. In particular, an input terminal 140 of an amplifier 136 is coupled to the cavity member 124 as indicated at 170, whilst an output stub coupler 150 is coupled to an output terminal 148 of a limiter 138 via a waveguide 149 and extends from a position on a surface of a distal end 154 in a generally radial direction with respect to an axis of the bore 106 of the fluid conduit 102. The waveguide 149 and the output stub coupler 150 are electrically insulated from the cavity member 124. Such a coupling arrangement may provide an enhancement in coupling with an electromagnetic field in the cavity 126 and, therefore, enhance measurement sensitivity for particular cavity configurations, fluids and/or fluid flow conditions in the bore 106 when compared with the coupling arrangement of the first embodiment shown in FIG. 3.

Figure 5:
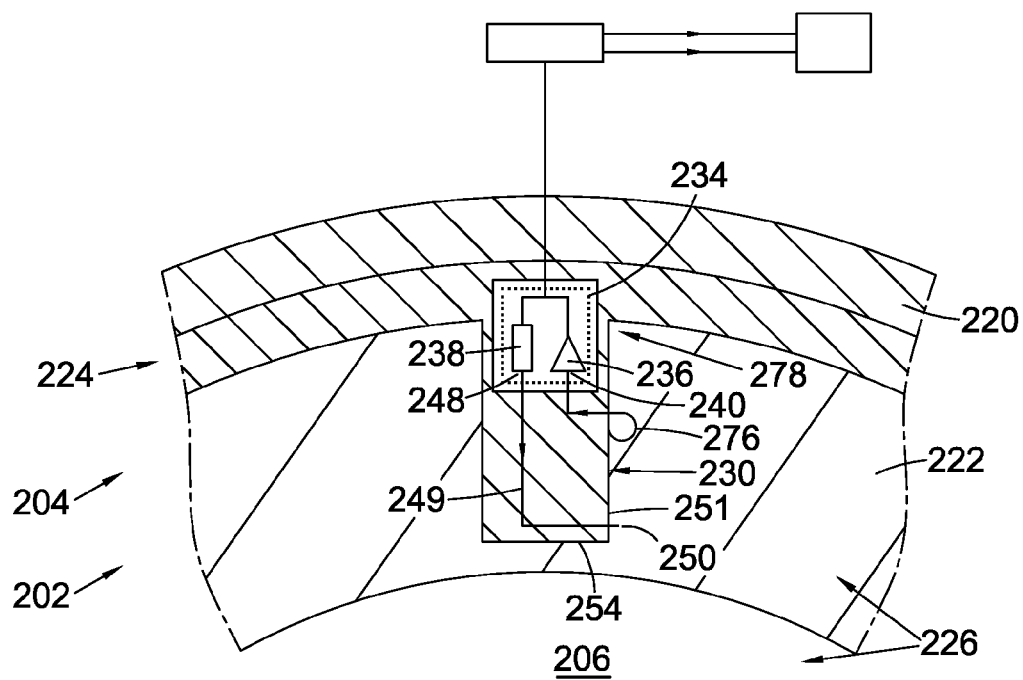
FIG. 5 is a detailed lateral cross-section of a field coupling region of a wall of a third fluid conduit embodiment.

FIG. 5 shows a detailed lateral cross-section of a field coupling region of a wall 204 of a fluid conduit generally designated 202 constituting a third embodiment of the present invention. The fluid conduit 202 of FIG. 5 shares many like features with the fluid conduit 2 of the first embodiment already described with reference to FIGS. 1-3. As such, the features of the fluid conduit 202 are identified with the same reference numerals used for the corresponding features of the fluid conduit 2 but incremented by "200". Like the fluid conduit 2 of FIGS. 1-3, the fluid conduit 202 of FIG. 5 comprises a wall 204 having a homogeneous region 222 (for example, a matrix material devoid of reinforcing fibres) which defines a bore 206 for fluid flow. The fluid conduit 202 also comprises a cavity member 224 embedded in the homogeneous region 222 so as to define a cavity 226 for an electromagnetic field. The fluid conduit 202 of FIG. 5 differs from the fluid conduit 2 of FIGS. 1-3 only in the coupling arrangement between a positive feedback arrangement 234 and the electromagnetic field in the cavity 226. In particular, an input terminal 240 of an amplifier 236 is coupled to a cylindrical surface 251 of a projecting portion 230 of the cavity member 224 via an inductive loop coupler 276 located towards a base portion 278 of the projecting portion 230, whilst a stub coupler 250 is coupled to an output terminal 248 of a limiter 238 via a waveguide 249 and extends from a position on the cylindrical surface 251 adjacent to a distal end 254 of the projecting portion 230 in a generally lateral direction with respect to the projecting portion 230. The waveguide 249 and the output stub coupler 250 are electrically insulated from the cavity member 224. Use of such an inductive loop coupler 276 may provide enhanced coupling with a magnetic field component of an electromagnetic field induced within the projecting portion 230 of the cavity member 224. This may provide enhanced measurement sensitivity for particular cavity configurations, fluids and/or fluid flow conditions in the bore 206 when compared with the coupling arrangement of the first embodiment shown in FIG. 3.

Figure 6:
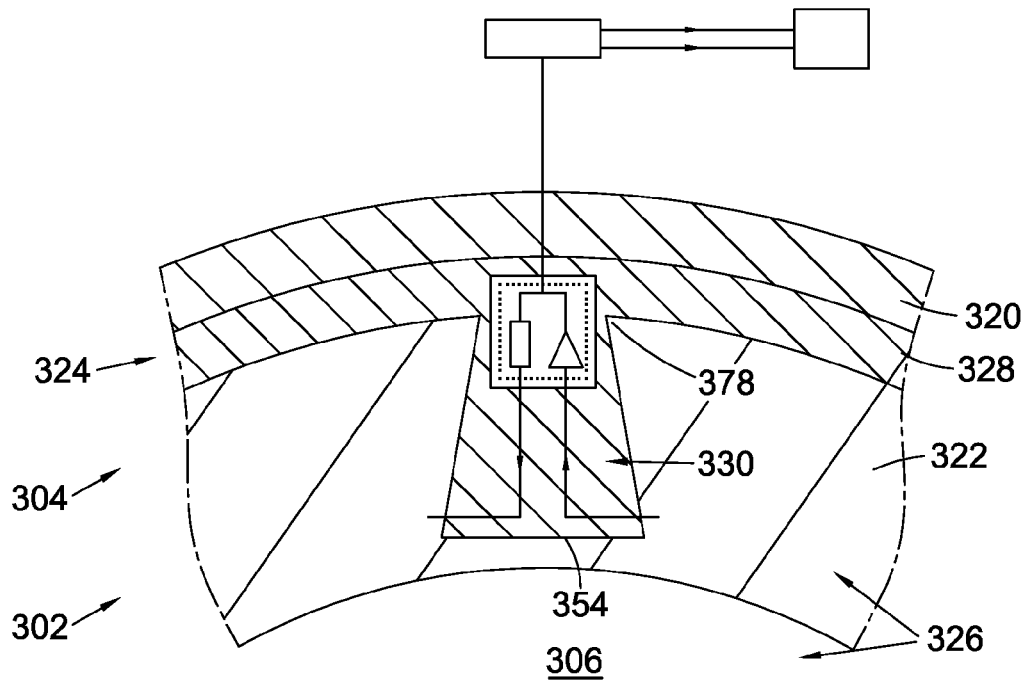
FIG. 6 is a detailed lateral cross-section of a field coupling region of a wall of a fourth fluid conduit embodiment.

FIG. 6 shows a detailed lateral cross-section of a field coupling region of a wall 304 of a fluid conduit generally designated 302 constituting a fourth embodiment of the present invention. The fluid conduit 302 of FIG. 6 shares many like features with the fluid conduit 2 of the first embodiment already described with reference to FIGS. 1-3. As such, the features of the fluid conduit 302 are identified with the same reference numerals used for the corresponding features of the fluid conduit 2 but incremented by "300". Like the fluid conduit 2 of FIGS. 1-3, the fluid conduit 302 of FIG. 6 comprises a wall 304 having a homogeneous region 322 (for example, a matrix material devoid of reinforcing fibres) which defines a bore 306 for fluid flow. The fluid conduit 302 also comprises a cavity member 324 embedded in the homogeneous region 322 so as to define a cavity 326 for an electromagnetic field. The fluid conduit 302 of FIG. 6 differs from the fluid conduit 2 of FIGS. 1-3 only in shape of a projecting portion 330 of the cavity member 324. As shown in FIG. 6, the projecting portion 330 is generally re-entrant so as to have an enlarged distal end 354 relative to a base 378 by which the projecting portion 330 is attached to an outer portion 328 of the cavity member 324. Such a configuration of the projecting portion 330 may provide an enhanced electric field component of the electromagnetic field within the cavity 326 in the vicinity of the distal end 354 and the base 378 when compared with the electric field component of the electromagnetic field within the cavity 26 in the vicinity of the stub couplers 42, 50 of the first embodiment shown in FIG. 3. This may provide enhanced measurement sensitivity for particular cavity configurations, fluids and/or fluid flow conditions in the bore 306 when compared with the coupling arrangement of the first embodiment shown in FIG. 3. As will be appreciated by one skilled in the art, other configurations of the projecting portion 330 are also possible in which the distal end 354 is enlarged relative to the base 378.

Figure 7:
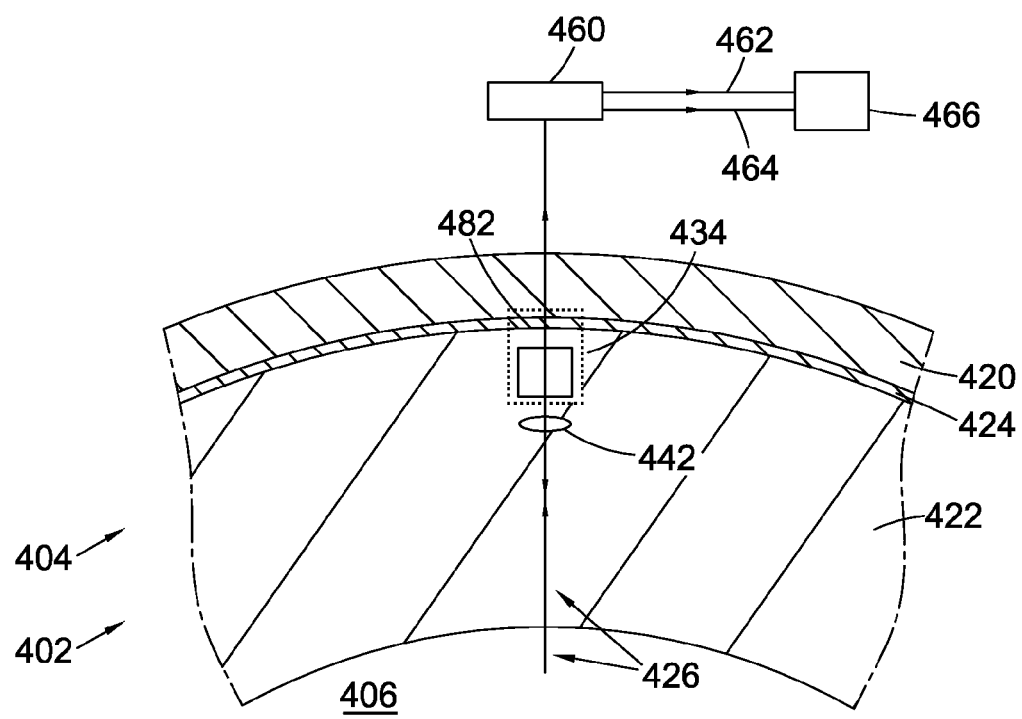
FIG. 7 is a detailed lateral cross-section of a field coupling region of a wall of a fifth fluid conduit embodiment.

FIG. 7 shows a detailed lateral cross-section of a field coupling region of a wall 404 of a fluid conduit generally designated 402 constituting a fifth embodiment of the present invention. The fluid conduit 402 of FIG. 7 shares many like features with the fluid conduit 2 of the first embodiment already described with reference to FIGS. 1-3. As such, the features of the fluid conduit 402 are identified with the same reference numerals used for the corresponding features of the fluid conduit 2 but incremented by "400". Like the fluid conduit 2 of FIGS. 1-3, the fluid conduit 402 of FIG. 7 comprises a wall 404 having a homogeneous region 422 (for example, a matrix material devoid of reinforcing fibres) which defines a bore 406 for fluid flow. The fluid conduit 402 also comprises an optically reflective cavity member 424 embedded in the homogeneous region 422 so as to define an optical cavity 426 that extends generally diametrically across the bore 406. The fluid conduit 402 of FIG. 7 differs from the fluid conduit 2 of FIGS. 1-3 in that the cavity member 424 has no projecting portion and the fluid conduit 402 comprises a positive feedback arrangement 434 defined by an optical gain medium 480 located within the wall 404 of the fluid conduit 402 and a portion 482 of the cavity member 424 in the vicinity of the optical gain medium 480. Also located within the hollow portion 432 is a lens 442 for collimating and/or conditioning an optical beam. The cavity member 424, the optical gain medium 480 and the lens 442 together define a laser. The portion 482 of the cavity member 424 in the vicinity of the optical gain medium 480 is configured to be only partially reflecting such that a fraction of the light circulating in the cavity 426 escapes from the cavity 426 in the region of the portion 482 of the cavity member 424. Light escaping from the cavity 426 is transmitted to an optical spectrum analyser device 460 either as a beam or via an optical waveguide such as an optical fibre (not shown). The optical spectrum analyser device 460 provides an output signal 462 representative of a resonant frequency of the optical cavity 426 and an output signal 464 representative of an electromagnetic loss in the optical cavity 426. This may provide enhanced measurement sensitivity for particular cavity configurations, fluids and/or fluid flow conditions in the bore 406 when compared with the coupling arrangement of the first embodiment shown in FIG. 3.

Figure 8:
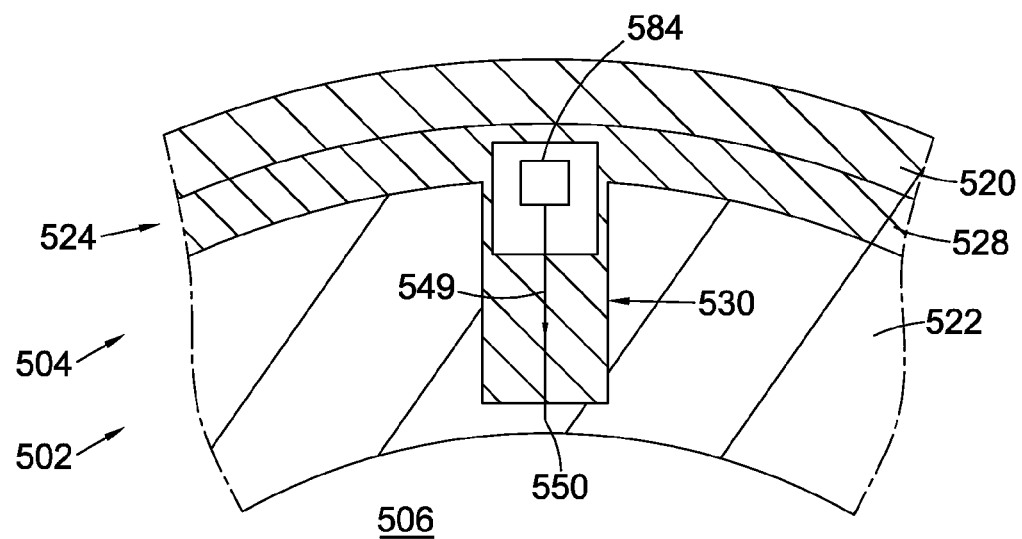
FIG. 8 is a detailed lateral cross-section of a field coupling region of a wall of a sixth fluid conduit embodiment.

FIG. 8 shows a detailed lateral cross-section of a field coupling region of a wall 504 of a fluid conduit generally designated 502 constituting a sixth embodiment of the present invention. The fluid conduit 502 of FIG. 8 shares many like features with the fluid conduit 2 of the first embodiment already described with reference to FIGS. 1-3. As such, the features of the fluid conduit 502 are identified with the same reference numerals used for the corresponding features of the fluid conduit 2 but incremented by "500". Like the fluid conduit 2 of FIGS. 1-3, the fluid conduit 502 of FIG. 8 comprises a wall 504 having a homogeneous region 522 (for example, a matrix material devoid of reinforcing fibres) which defines a bore 506 for fluid flow. The fluid conduit 502 also comprises a cavity member 524 embedded in the homogeneous region 522 so as to define a cavity 526 for an electromagnetic field. The fluid conduit 502 of FIG. 8 differs from the fluid conduit 2 of FIGS. 1-3 in that rather than comprising a positive feedback arrangement, the fluid conduit 502 comprises an electromagnetic source 584 housed within a hollow portion 532 of the wall 504 of the fluid conduit 502. An output of the RF source is coupled via a waveguide 549 to an output stub coupler 550 for coupling electromagnetic energy from the electromagnetic source to an electric field component of the electromagnetic field within the cavity 526. The waveguide 549 and the output stub coupler 550 are electrically insulated from the cavity member 524. Unlike the cavity 26 of the fluid conduit 2 of FIGS. 1-3, however, the cavity 526 is non-resonant and feedback of energy from the electromagnetic field to the electromagnetic source 584 via the output stub coupler 550 and the waveguide 549 is minimized. Put another way, the cavity member 524 functions to contain the energy of the electromagnetic field rather than feeding energy from the electromagnetic field back to the electromagnetic source 584. The fluid conduit 502 of FIG. 8 may be used to create an electromagnetic field in the cavity 526 and thereby expose the fluid to the electromagnetic field. Such an arrangement may be used to transfer energy to the fluid, for example, for heating the fluid.

Figure 9:
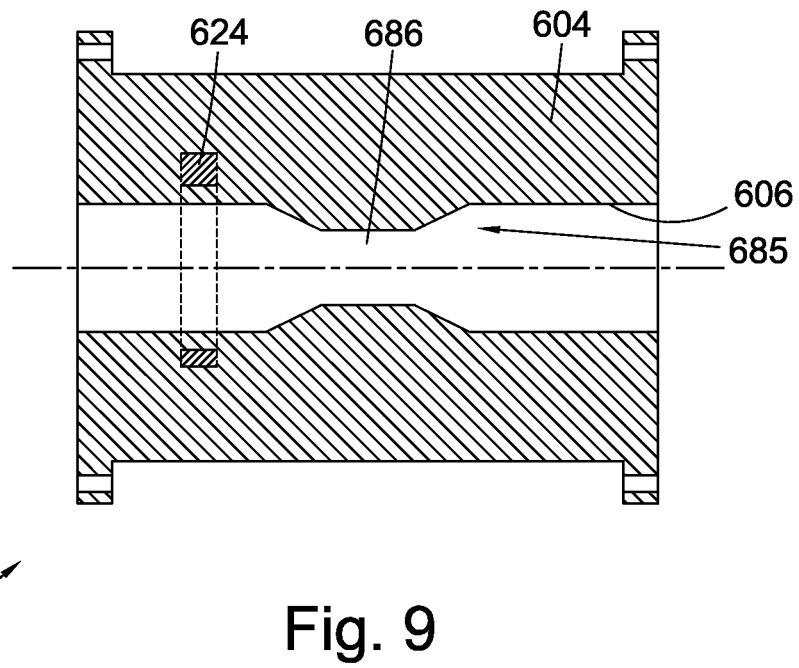
FIG. 9 is a longitudinal cross-section of a fluid conduit constituting a seventh fluid conduit embodiment.

FIG. 9 shows a longitudinal cross-section of a fluid conduit generally designated 602 constituting a seventh embodiment of the present invention. The fluid conduit 602 of FIG. 9 shares many like features with the fluid conduit 2 of the first embodiment already described with reference to FIGS. 1-3. As such, the features of the fluid conduit 602 are identified with the same reference numerals used for the corresponding features of the fluid conduit 2 but incremented by "600". Like the fluid conduit 2 of FIGS. 1-3, the fluid conduit 602 of FIG. 9 comprises a wall 604 which defines a bore 606 for fluid flow. The fluid conduit 602 also comprises a cavity member 624 embedded in the wall 604 so as to define a cavity 626 for an electromagnetic field. The fluid conduit 602 of FIG. 9 differs from the fluid conduit 2 of FIGS. 1-3 in that the fluid conduit 602 also comprises a Venturi effect flow rate sensor generally designated 685 which comprises a restricted portion 686 of the bore 606 and one or more pressure sensors (not shown). Each of the pressure sensors (not shown) may comprise a strain gauge, a piezoelectric sensor, a capacitive, optical, or magnetic pressure sensor, a pressure gauge or a pressure sensor of any other kind. The pressure sensors may be configured to measure a pressure of a fluid in the bore 606 directly or to measure a pressure of a fluid in the bore 606 indirectly by measuring the effects of fluid pressure on the wall 604 of the fluid conduit 602.

Figure 10:
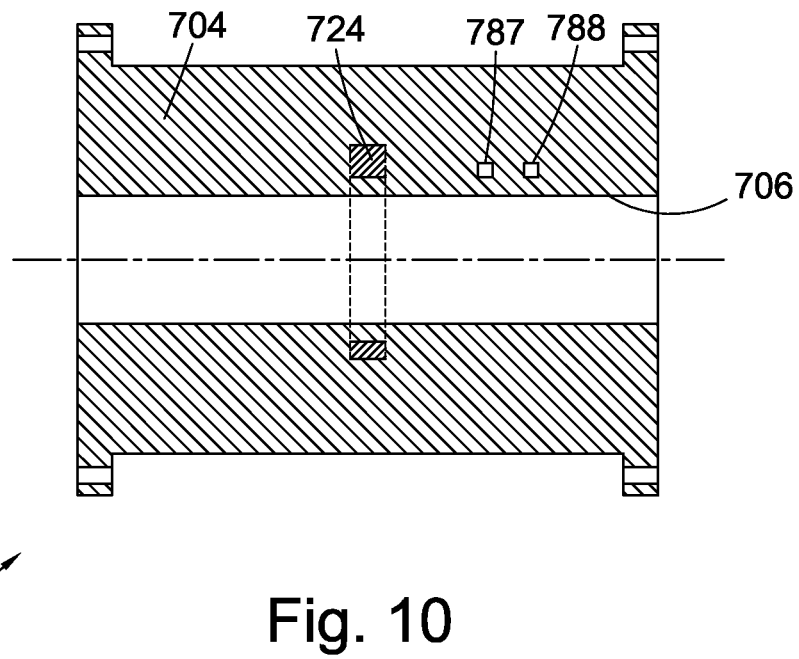
FIG. 10 is a longitudinal cross-section of a fluid conduit constituting an eighth fluid conduit embodiment.

FIG. 10 shows a longitudinal cross-section of a fluid conduit generally designated 702 constituting an eighth embodiment of the present invention. The fluid conduit 702 of FIG. 10 shares many like features with the fluid conduit 2 of the first embodiment already described with reference to FIGS. 1-3. As such, the features of the fluid conduit 702 are identified with the same reference numerals used for the corresponding features of the fluid conduit 2 but incremented by "700". Like the fluid conduit 2 of FIGS. 1-3, the fluid conduit 702 of FIG. 10 comprises a wall 704 which defines a bore 706 for fluid flow. The fluid conduit 702 also comprises a cavity member 724 embedded in the wall 704 so as to define a cavity 726 for an electromagnetic field. The fluid conduit 702 of FIG. 10 differs from the fluid conduit 2 of FIGS. 1-3 in that the fluid conduit 702 also comprises a temperature sensor 787 embedded within the wall 704 and a pressure sensor 788 embedded within the wall 704. The temperature sensor 787 may comprise a resistance temperature detector (RTD), a thermistor, a thermocouple of the like. The pressure sensor 788 may comprise a strain gauge, a piezoelectric sensor, a capacitive, optical, or magnetic pressure sensor, a pressure gauge or a pressure sensor of any other kind. The pressure sensor 788 may be configured to measure a pressure of a fluid in the bore 706 directly or to measure a pressure of a fluid in the bore 706 indirectly by measuring the effects of fluid pressure on the wall 704 of the fluid conduit 702. In use, such temperature and pressure sensors 787, 788 may assist in resolving a fluid or composition of a fluid present in or flowing through the bore 706.

Figure 11A:
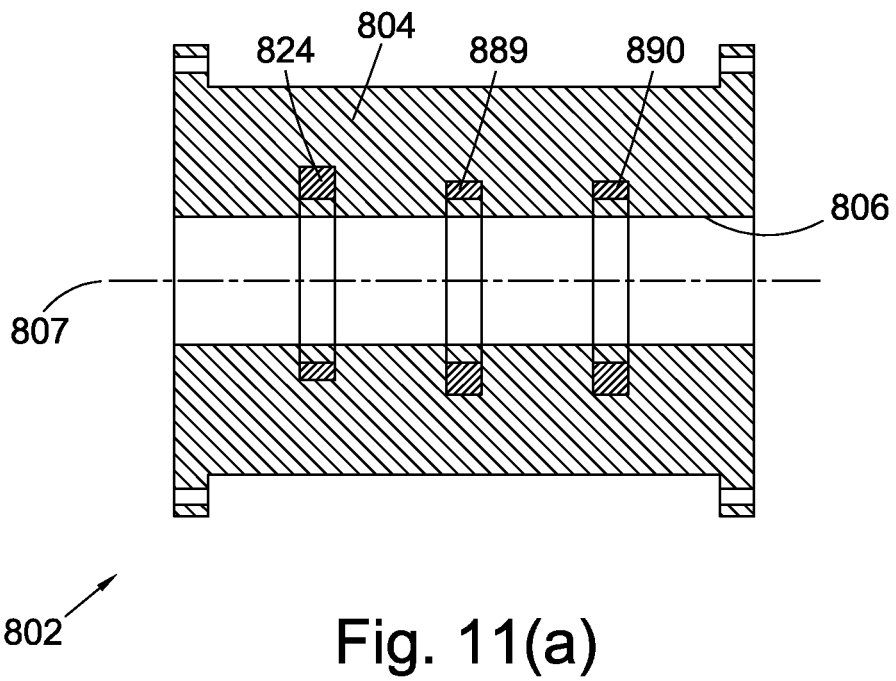
FIG. 11(a) is a longitudinal cross-section of a fluid conduit constituting a ninth fluid conduit embodiment.
Figure 11B:
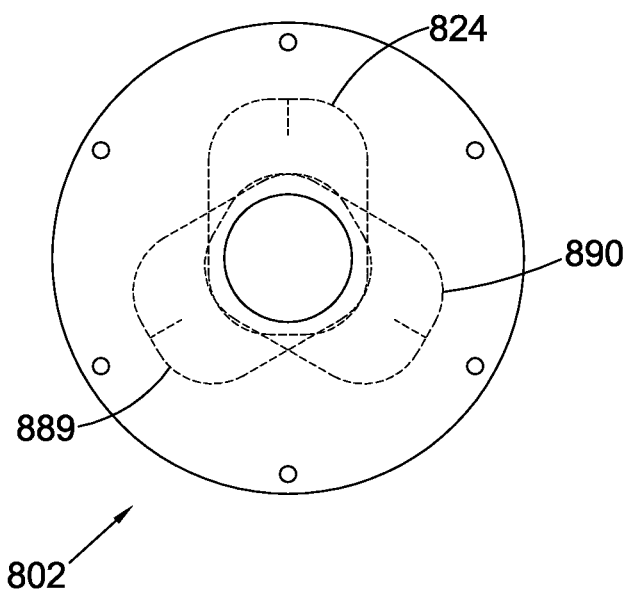
FIG. 11(b) is an end elevation of the fluid conduit of FIG. 11(a)

FIG. 11(*a*) shows a longitudinal cross-section of a fluid conduit generally designated 802 constituting a ninth embodiment of the present invention. The fluid conduit 802 of FIG. 11 shares many like features with the fluid conduit 2 of the first embodiment already described with reference to FIGS. 1-3. As such, the features of the fluid conduit 802 are identified with the same reference numerals used for the corresponding features of the fluid conduit 2 but incremented by "800". Like the fluid conduit 2 of FIGS. 1-3, the fluid conduit 802 of FIG. 11(*a*) comprises a wall 804 which defines a bore 806 for fluid flow. The fluid conduit 802 also comprises a cavity member 824 embedded in the wall 804 so as to define a cavity 826 for an electromagnetic field. The fluid conduit 802 of FIG. 11(*a*) differs from the fluid conduit 2 of FIGS. 1-3 in that the fluid conduit 802 comprises two additional cavity members 889 and 890 embedded in the wall 804. The cavity members 824, 889 and 890 are separated axially along the bore 806. As indicated in FIG. 11(*b*), the cavity members 824, 889 and 890 are each orientated about an axis 807 of the bore 806 so as to have a uniform angular distribution in which each cavity member 824, 889, 890 is separated from adjacent cavity members 824, 889, 890 by an angle of 120°. Such an arrangement of the cavity members 824, 889, 890 may improve the sensitivity with which a fluid or composition of a fluid present in or flowing through the bore 706 may be resolved.

Figure 12:
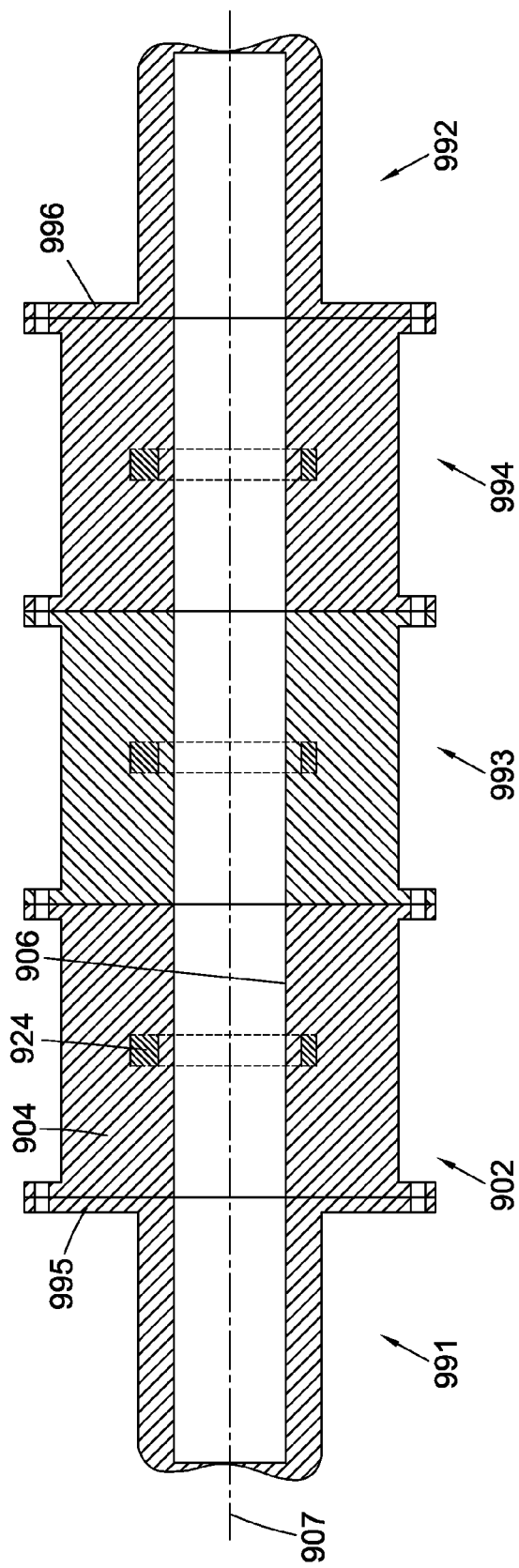
FIG. 12 is a longitudinal cross-section of a portion of a pipeline comprising two pipe lengths having enlarged flanges and a plurality of fluid conduits.

FIG. 12 shows a longitudinal cross-section of a portion of a pipeline comprising two pipe lengths 991 and 992 having enlarged flanges 995 and 996 respectively, a fluid conduit generally designated 902 and two additional fluid conduits generally designated 993 and 994. The fluid conduit 902 of FIG. 12 shares many like features with the fluid conduit 2 of the first embodiment already described with reference to FIGS. 1-3. As such, the features of the fluid conduit 902 are identified with the same reference numerals used for the corresponding features of the fluid conduit 2 but incremented by "900". Like the fluid conduit 2 of FIGS. 1-3, the fluid conduit 902 of FIG. 12 comprises a wall 904 which defines a bore 906 for fluid flow. The fluid conduit 902 also comprises a cavity member 924 embedded in the wall 904 so as to define a cavity 926 for an electromagnetic field. The fluid conduits 902, 993 and 994 are separately axially along the bore 906 and have the same general orientation about an axis 907 of the bore 906. The fluid conduits 902, 993 and 994 differ from one another only in that each fluid conduit 902, 993 and 994 is tuned so as to be resonant at a different frequency or over a range of different frequencies. This may be achieved by providing each fluid conduit 902, 993 and 994 with a differently configured cavity member or providing each fluid conduit 902, 993 and 994 with a wall of a different configuration or composition. Such a pipeline may improve the sensitivity with which a fluid or composition of a fluid present in or flowing through the bore 906 may be resolved. Additionally or alternatively, such a pipeline may assist in the sensing, determination and/or measurement of one or more additional fluid components in a fluid present in or flowing through the bore 906 when compared with a pipeline comprising only a single fluid conduit such as fluid conduit 902.

Figure 13:
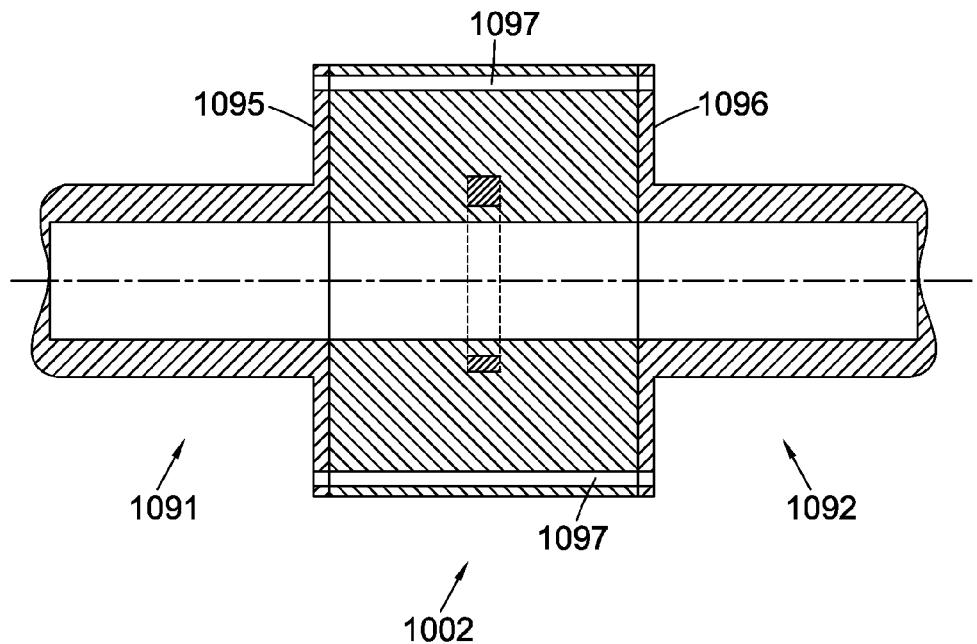
FIG. 13 is a longitudinal cross-section of a portion of a pipeline comprising two pipe lengths having enlarged flanges and a fluid conduit having through holes extending along the length of the fluid conduit for attachment to the enlarged flanges of the pipe lengths.

FIG. 13 shows a longitudinal cross-section of a portion of a pipeline comprising two pipe lengths 1091 and 1092 having enlarged flanges 1095 and 1096 respectively and a fluid conduit generally designated 1002 having through holes 1097 extending along the length of the fluid conduit 1002 for attachment to the enlarged flanges 1095, 1096 of the pipe lengths 1091 and 1092. Such an arrangement of the through holes 1097 may be advantageous because it avoids the requirement to form flanges at the ends of the fluid conduit 1002 for attachment to the pipe lengths 1091 and 1092.

Figure 14:
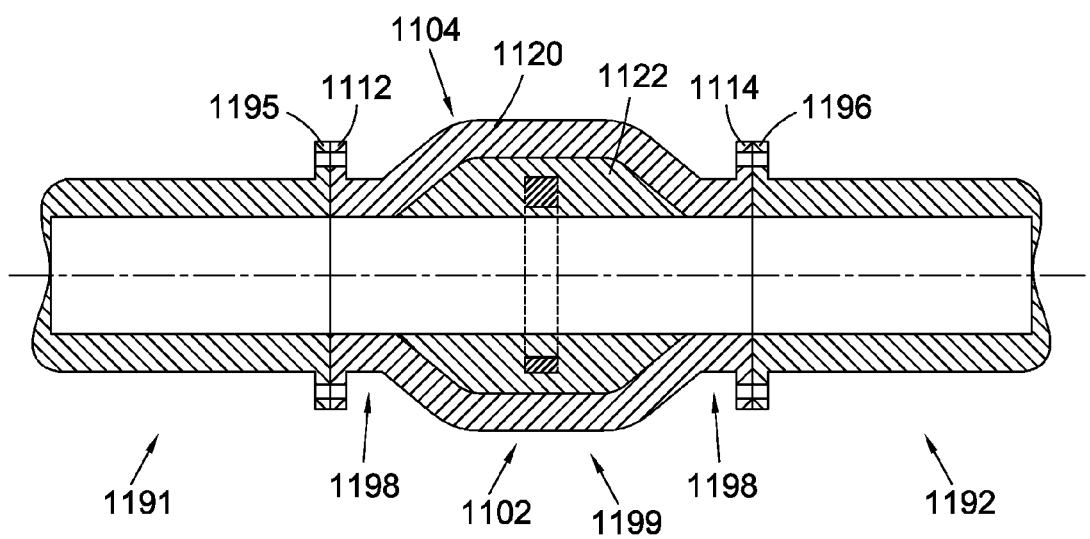
FIG. 14 is a longitudinal cross-section of a portion of a pipeline comprising two standard pipe lengths and a fluid conduit having axial end portions comprising flanges each configured for attachment to a corresponding flange of a standard pipe length.

FIG. 14 shows a longitudinal cross-section of a portion of a pipeline comprising two standard-sized pipe lengths 1191 and 1192 having standard-sized flanges 1195 and 1196 respectively and a fluid conduit generally designated 1102 having standard-sized flanges 1112 and 1114 for attachment to the standard-sized flanges 1195 and 1196 of the pipe lengths 1191 and 1192. The fluid conduit 1102 of FIG. 14 shares many like features with the fluid conduit 2 of the first embodiment already described with reference to FIGS. 1-3. As such, the features of the fluid conduit 1102 are identified with the same reference numerals used for the corresponding features of the fluid conduit 2 but incremented by "1100". Like the fluid conduit 2 of FIGS. 1-3, the fluid conduit 1102 of FIG. 14 comprises a wall 1104 which defines a bore 1106 for fluid flow. The fluid conduit 1102 also comprises a cavity member 1124 embedded in the wall 1104 so as to define a cavity 1126 for an electromagnetic field. In contrast to the fluid conduit 2 of FIGS. 1-3, however, the fluid conduit 1102 of FIG. 14 comprises two axial end portions generally designated 1198 adjacent to the flanges 1112 and 1114, and an axial middle portion generally designated 1199 between the axial end portions 1998. In the axial middle portion 1199, the wall 1104 comprises a composite region 1120 and a homogeneous region 1122 which defines the bore 1106. The composite region 1120 comprises a matrix of a polyether ether ketone (PEEK) and a plurality of reinforcing elements in the form of carbon fibres (not shown explicitly) embedded within the PEEK. The homogeneous region 1122 comprises PEEK and is devoid or at least substantially devoid of any reinforcing elements at a microscopic level. The PEEK material of regions 1120 and 1122 defines a monolithic structure and extends continuously between said regions. Accordingly, it may be considered that the entire wall 1104 is of a composite construction of a matrix and reinforcing elements, wherein region 1122 is substantially devoid of reinforcing elements.

In the axial end portions 1998 the wall comprises only a composite region 1120. In the axial middle portion 1199, the wall 1104 has an outer diameter which is greater than an outer diameter of the wall 1104 in the axial end portions 1998 so that the axial middle portion 1199 may accommodate the homogeneous region 1122 and the cavity member 1124 embedded therein. Such a fluid conduit 1102 may be advantageous because it may be connected between standard-sized pipe lengths having standard-sized flanges and therefore avoids any need to adapt the pipe lengths to permit connection of the fluid conduit 1102.

Figure 15:
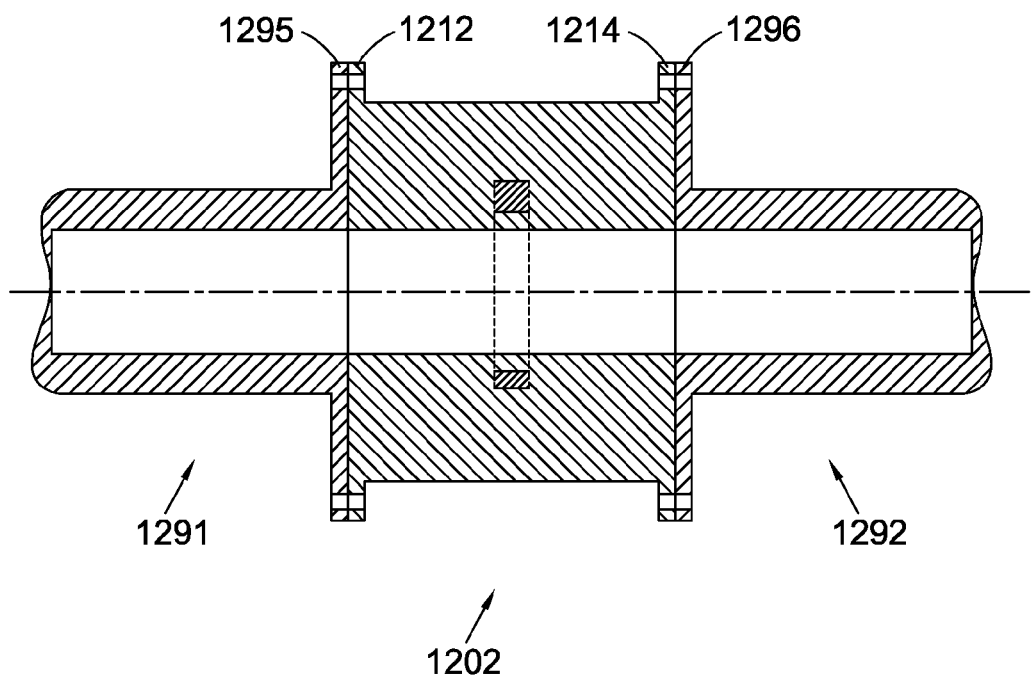
FIG. 15 is a longitudinal cross-section of a portion of a pipeline comprising two pipe lengths having enlarged flanges and a fluid conduit.
Figure 16B:
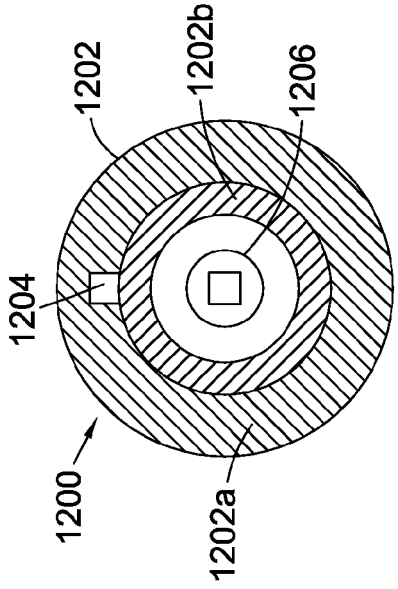
FIGS. 16 (a) to (d) are lateral cross-sectional views of various embodiments of a fluid conduit in accordance with one or more aspects of the present invention.
Figure 16D:
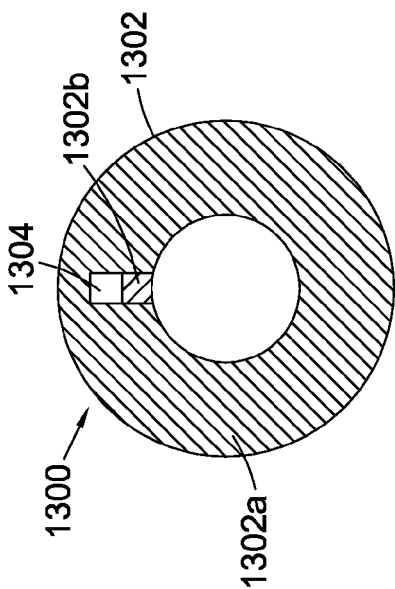
Figure 16A:
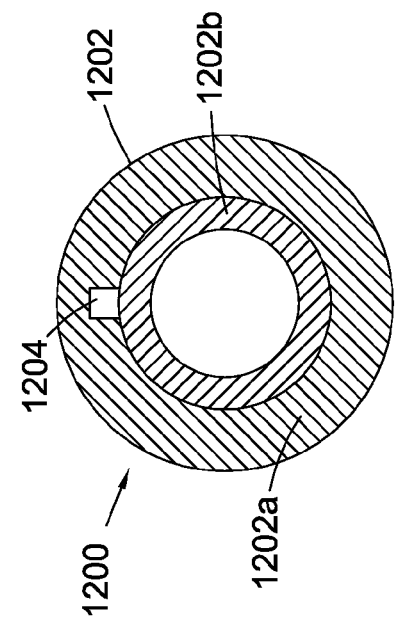
Figure 16C:
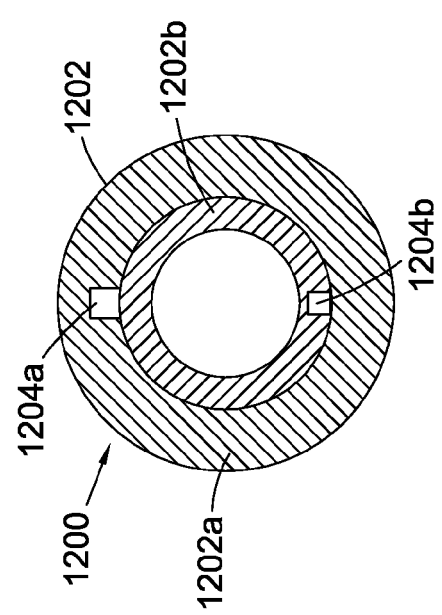

FIG. 15 shows a longitudinal cross-section of a portion of a pipeline comprising two standard-sized pipe lengths 1291 and 1292 having enlarged flanges 1295 and 1296 respectively and a fluid conduit generally designated 1202 having flanges 1212 and 1214 for attachment to the enlarged flanges 1295 and 1296 of the pipe lengths 1291 and 1292. The fluid conduit 1202 of FIG. 15 differs from the fluid conduit 1102 of FIG. 14 in that the fluid conduit 1202 of FIG. 15 requires the flanges 1295 and 1296 of the pipe lengths 1291 and 1292 to be enlarged to permit connection to the larger diameter of the fluid conduit 1202. The enlarged flanges 1295 and 1296 of the pipe lengths 1291 and 1292 may, for example, be formed by welding over-sized flange components onto the ends of the pipe lengths 1291 and 1292.

An alternative embodiment of the present invention is illustrated in FIG. 16(*a*) in which a cross sectional view of a fluid conduit, generally identified by reference numeral 1200, is shown. The conduit 1200 includes a wall 1202 which defines a flow path 1203. The wall 1202 is formed of an outer region 1202*a* formed of a composite material which includes reinforcing elements embedded within a matrix, and an inner region 1202*b* of a general homogeneous construction which is substantially devoid of reinforcing elements. The homogeneous region 1202*b* may be formed of the matrix material which is included in the outer composite region 1202*a*, such that said matrix may be considered to define a monolithic structure throughout the wall 1202.

A component 1204 is embedded within the wall 1202 of the conduit 1200 at a location such that the homogenous region 1202*b* extends between the component 1204 and flow path 1203. The component may be arranged to transmit energy to and/or receive energy from the flow path 1203, wherein the homogeneous region 1202*b* defines a transmission path. That is, the absence of reinforcing fibres within region 1202*b* may permit the energy to be transmitted with minimal interference.

In the illustrated embodiment the component 1204 defines a transceiver and is arranged to both transmit and receive energy. For example, energy may be transmitted into the flow path 1203 and pass through a fluid contained within or flowing therethrough, and then be received by the component 1204. The energy received may be used to determine a property of the fluid, such as its composition, type, flowrate, mass flow rate or the like. For example, a feature or component of the energy, such as an amplitude, frequency, wavelength or the like may become modified by the fluid, with such modification being indicative of a property of the fluid.

Alternatively, component 1204 may be arranged only to transmit energy to intentionally alter a property of the fluid, such as to encourage separation of different components, to heat the fluid or the like.

In a modified embodiment, as illustrated in FIG. 16(*b*), the component 1204 may be configured to either transmit or receive energy, wherein an inner tool 1206 is located within the flow path 1203 for either receiving or transmitting energy.

In a further modified embodiment, as illustrated in FIG. 16(*c*), the conduit 1200 may comprise multiple components 1204*a*, 1204*b* for appropriate transmission and receiving of energy. To illustrate a possible modification, a component (1204*b* in this example) may be embedded entirely within the inner homogenous region 1202*b*.

In the embodiments shown in FIGS. 16(*a*) to (*c*) the wall of the conduit is composed of inner an outer regions. However, an alternative to this is illustrated in FIG. 16(*d*), reference to which is now made. A conduit, generally identified by reference numeral 1300 includes a wall 1302 which defines a flow path 1303, and a component 1304 embedded within said wall 1302. The wall 1302 is constructed to include a composite region 1302*a* which includes reinforcing elements embedded within a matrix. The wall 1302 further includes a homogeneous region or segment 1302*b* which is substantially devoid of reinforcing elements and which extends only generally between the component 1304 and the flow path 1303. The homogeneous region 1302*b* may be formed of the matrix material which is included in composite region 1302*a*, such that said matrix may be considered to define a monolithic structure throughout the wall 1302.

In the various embodiments shown in FIGS. 16(*a*) to (*d*) the component may comprise at least one of a transducer, a sensor, a receiver, a transmitter, a transceiver, an antenna and confinement feature. The component may be configured for transmission and/or reception of acoustic energy, electromagnetic energy or the like.

One skilled in the art will understand that various modifications of the foregoing embodiments of the fluid conduit are possible without departing from the scope of the present invention. For example, rather than extending axially partway along the length of the fluid conduit 2 between the first and second ends 8, 10, the cavity member 24 may extend axially along the entire length of the fluid conduit 2.

The projecting portion 30 of the cavity member 24 of FIGS. 1-3 may have a geometry which is other than cylindrical. For example, the projecting portion 30 may have a uniform cross-section as shown in FIG. 3 and extend axially.

The positive feedback arrangement may comprise a negative resistance in place of the series arrangement of an RF amplifier and a limiter in the first to fourth embodiments of FIGS. 1-6.

In a variant of the second embodiment of FIG. 5, the input terminal 240 of the RF amplifier 236 may be coupled to the stub coupler 250 and the output terminal 248 of the limiter 238 may be coupled to the inductive loop coupler 276.

In a further embodiment, a confinement feature such as a cavity member may be embedded in a homogeneous region of the wall of a fluid conduit so as to define a cavity for an acoustic field. Additionally or alternatively, the confinement feature may comprise a hollow portion formed in the homogeneous region of the wall. A positive feedback arrangement may comprise an electronic amplifier arrangement for amplifying an electronic signal at an acoustic frequency and an acoustic transducer for transforming the electronic signal to an acoustic signal for coupling to an acoustic field within the bore for interaction with fluid present in or flowing through the bore. The electronic signal may be input to a demodulator for providing an output signal representative of a resonant frequency of the acoustic cavity and an output signal representative of a loss in the acoustic cavity.

In other embodiments, a confinement feature such as a cavity member or a hollow portion may be embedded in a homogeneous region of a wall of a fluid conduit so as to define a cavity for an acoustic field. Additionally or alternatively, the confinement feature may comprise a hollow portion formed in the homogeneous region of the wall. An acoustic source may be coupled to the acoustic field within the bore for interaction with fluid in the bore. Such an embodiment may be used to provide acoustic energy to fluid present in or flowing through the bore and may, in particular, be useful for agitating the fluid. This may be advantageous for mixing the fluid, breaking up any entrained solids in the fluid and/or for removal of any build-up or contaminants deposited within the bore of the fluid conduit.

In a variant of the ninth embodiment of FIGS. 11(a) and (b), rather than comprising three cavity members 824, 889 and 890, the fluid conduit 802 may comprise more or fewer cavity members. For example, the fluid conduit 802 may comprise two cavity members which are separated axially from one another. The two cavity members may be oriented about axis 807 at an angle with respect to one another. For example, the two cavity members may be oriented about axis 807 at an angle of 90° with respect to one another.

The invention claimed is:

1. A fluid conduit for use in imparting energy to a fluid present in or flowing therethrough, the fluid conduit comprising:
a wall defining a fluid flow path and comprising an outer layer of composite material formed of at least a matrix and one or more reinforcing elements embedded within the matrix and a homogeneous inner region devoid of reinforcing elements; and
a confinement feature embedded within the wall confining energy within a cavity, the cavity embedded within the homogeneous inner region of the wall, wherein at least a portion of the fluid flow path extends through the cavity.

2. The fluid conduit according to claim 1, wherein the matrix material defines a monolithic structure.

3. The fluid conduit according to claim 1, wherein the distribution or concentration of the reinforcing elements varies within the matrix.

4. The fluid conduit according to claim 1, wherein the concentration of the reinforcing elements increases with distance from the fluid flow path.

5. The fluid conduit according to claim 1, wherein a region of the wall adjacent to the fluid flow path is substantially devoid of reinforcing elements.

6. The fluid conduit according to claim 1, wherein a region of the wall between the confinement feature and the fluid flow path is substantially devoid of reinforcing elements.

7. The fluid conduit according to claim 1, wherein the wall comprises an inert region extending between the confinement feature and the fluid flow path, wherein the inert region is configured to transmit energy therethrough.

8. The fluid conduit according to claim 1, wherein the wall comprises a homogeneous region extending between the confinement feature and the fluid flow path, wherein the homogeneous region is substantially homogeneous at a microscopic level.

9. The fluid conduit according to claim 1, wherein the cavity member is at least partially enclosed or embedded within the composite material of the wall.

10. The fluid conduit according to claim 1, wherein the confinement feature is configured to confine electromagnetic energy, electric energy, magnetic energy, an electromagnetic field, an electric field, and/or a magnetic field.

11. The fluid conduit according to claim 1, wherein the confinement feature is configured to confine radio frequency, ultraviolet frequency, optical frequency, mm-wave frequency and/or microwave frequency electromagnetic energy and/or a radio frequency, an ultraviolet frequency, an optical frequency, a mm-wave frequency and/or a microwave frequency electromagnetic field.

12. The fluid conduit according to claim 1, wherein the confinement feature is configured to confine acoustic energy, an acoustic field, and/or a radioactive emission.

13. The fluid conduit according to claim 1, wherein the confinement feature is configured to partially, substantially or wholly confine energy within the cavity.

14. The fluid conduit according to claim 1, wherein the confinement feature at least partially defines the cavity.

15. The fluid conduit according to claim 1, wherein the confinement feature at least partially surrounds the fluid flow path.

16. The fluid conduit according to claim 1, wherein the confinement feature comprises a metal.

17. The fluid conduit according to claim 1, wherein the confinement feature comprises a cavity member which is separately formed from the wall.

18. The fluid conduit according to claim 1, wherein the cavity is configured to be resonant at a predetermined frequency or over a predetermined range or frequencies.

19. The fluid conduit according to claim 1, comprising a coupling element for coupling energy to and/or from the cavity.

20. The fluid conduit according to claim 19, wherein the coupling element is at least partially recessed, enclosed or embedded within the wall.

21. The fluid conduit according to claim 1, wherein the wall is configured to transmit energy between the confinement feature and the fluid flow path.

22. The fluid conduit according to claim 1, wherein the wall is configured to have a negligible or relatively insignificant effect on the transmission of energy between the confinement feature and the fluid flow path.

23. The fluid conduit according to claim 1, wherein the wall is configured to affect an energy field in the cavity in a known or quantifiable manner.

24. The fluid conduit according to claim 1, wherein the wall is substantially homogeneous at a microscopic level.

25. The fluid conduit according to claim 1, wherein the matrix comprises at least one of a polymer material, a thermoplastic material, a thermoset material, a polyaryl ether ketone, a polyaryl ketone, a polyether ketone (PEK), a polyether ether ketone (PEEK), a polycarbonate, a polymeric resin, and/or an epoxy resin.

26. The fluid conduit according to claim 1, wherein the reinforcing elements comprise continuous elements, discontinuous elements, strands, filaments, nanotubes, fibres, polymeric fibres, aramid fibres, non-polymeric fibres, carbon fibres, glass fibres and/or basalt fibres.

27. The fluid conduit according to claim 1, comprising an arrangement for generating energy.

28. The fluid conduit according to claim 1, comprising a positive feedback arrangement.

29. The fluid conduit according to claim 28, comprising an oscillator defined by the cavity and the positive feedback arrangement.

30. The fluid conduit according to claim 29, comprising an output arranged to provide a signal that varies according to a value of a resonant frequency and/or a loss of the oscillator.

31. The fluid conduit according to claim 1, comprising an energy source, a source of electromagnetic energy, a source of acoustic energy and/or a radioactive source.

32. The fluid conduit according to claim 1, comprising at least one of a temperature sensor and a pressure sensor at least partially recessed, enclosed or embedded within the wall of the fluid conduit.

33. The fluid conduit according to claim 1, comprising a sensor configured to sense flow rate within the fluid flow path.

34. The fluid conduit according to claim 1, comprising a plurality of confinement features within the wall, each confinement feature configured to confine energy within a corresponding cavity, wherein each cavity is configured to be resonant at a different frequency or over a different range of frequencies.

35. The fluid conduit according to claim 1, comprising one or more through holes that extend along a length of the fluid conduit, the through holes being configured for attachment of the fluid conduit to a respective pipe length located at either end of the fluid conduit via fasteners which extend through the through holes.

36. A pipeline for a fluid comprising: one or more lengths of pipe; and a fluid conduit according to claim 1.

* * * * *